United States Patent
Holschuh et al.

(10) Patent No.: US 10,828,221 B2
(45) Date of Patent: Nov. 10, 2020

(54) WEARABLE, SELF-LOCKING SHAPE MEMORY ALLOY (SMA) ACTUATOR CARTRIDGE

(71) Applicant: Massachusetts Institute of Technology, Cambridge, MA (US)

(72) Inventors: Bradley T. Holschuh, North Oaks, MN (US); Dava J. Newman, Marblehead, MA (US); Giacomo Gatto, Rome (IT); Luca Levrino, Turin (IT)

(73) Assignee: Massachusetts Institute of Technology, Cambridge, MA (US)

( * ) Notice: Subject to any disclaimer, the term of this patent is extended or adjusted under 35 U.S.C. 154(b) by 838 days.

(21) Appl. No.: 15/518,356

(22) PCT Filed: Nov. 5, 2015

(86) PCT No.: PCT/US2015/059253
§ 371 (c)(1),
(2) Date: Apr. 11, 2017

(87) PCT Pub. No.: WO2016/077150
PCT Pub. Date: May 19, 2016

(65) Prior Publication Data
US 2017/0304136 A1    Oct. 26, 2017

Related U.S. Application Data

(60) Provisional application No. 62/079,779, filed on Nov. 14, 2014.

(51) Int. Cl.
*A61H 1/00* (2006.01)
*A41D 31/00* (2019.01)
(Continued)

(52) U.S. Cl.
CPC ............. *A61H 1/008* (2013.01); *A41D 31/00* (2013.01); *A61F 5/028* (2013.01); *A61F 5/03* (2013.01);
(Continued)

(58) Field of Classification Search
CPC ........ A61B 2017/00867; A61B 17/132; A61B 17/1322; A61B 17/1327; A61B 17/135;
(Continued)

(56) References Cited

U.S. PATENT DOCUMENTS 5,641,955 A    6/1997 Bonniau et al.
5,997,465 A    12/1999 Savage et al.
(Continued)

FOREIGN PATENT DOCUMENTS

DE    19529500 A1    2/1997
GB    2 441 589 A    3/2008
(Continued)

OTHER PUBLICATIONS

PCT Search Report and Written Opinion of the ISA for PCT/US2015/059253 dated Jan. 13, 2016; 12 Pages.
(Continued)

*Primary Examiner* — Samchuan C Yao
*Assistant Examiner* — Matthew Standard
(74) *Attorney, Agent, or Firm* — Daly, Crowley, Mofford & Durkee LLP

(57) ABSTRACT

Described embodiments provide a shape memory alloy (SMA) cartridge for use in providing controllable compression. The SMA cartridge includes first and second end caps, each of the first and second end caps being coupled to a passive material. One or more SMA coils extend between the first and second end caps. The SMA coils have a trained state and a deformed state, where the SMA coils are in the deformed state when a stimulus is provided thereto and the
(Continued)

SMA coils are in the trained state when the stimulus is removed therefrom. The first end cap and the second end cap include a locking mechanism to automatically lock the first and second end caps in a fixed position relative to one another when the SMA coils are contracted.

24 Claims, 25 Drawing Sheets

(51) Int. Cl.
    *A61F 5/02*     (2006.01)
    *A61F 5/03*     (2006.01)
(52) U.S. Cl.
    CPC .... *A41D 2400/32* (2013.01); *A61H 2201/165* (2013.01); *A61H 2205/10* (2013.01); *A61H 2209/00* (2013.01)
(58) Field of Classification Search
    CPC ............. A61B 17/1355; A63B 2209/14; A61F 2210/0014; A61H 1/008; A61H 2201/165; A61H 9/005–0092
    See application file for complete search history.

(56) References Cited

U.S. PATENT DOCUMENTS

| | | | |
|---|---|---|---|
| 6,006,522 | A | 12/1999 | Foss, Jr. et al. |
| 6,010,471 | A | 1/2000 | Ben-Noon |
| 6,389,200 | B1 | 5/2002 | Foltzer |
| 7,413,622 | B2 | 6/2008 | Peterson |
| 9,328,266 | B2 | 5/2016 | Vanimisetti et al. |
| 2002/0052568 | A1 | 5/2002 | Houser et al. |
| 2002/0074901 | A1 | 6/2002 | Johansson |
| 2003/0059640 | A1 | 3/2003 | Marton et al. |
| 2003/0125781 | A1 | 7/2003 | Dohno et al. |
| 2005/0043657 | A1 | 2/2005 | Couvillon, Jr. |
| 2006/0287621 | A1 | 12/2006 | Atkinson et al. |
| 2008/0057809 | A1 | 3/2008 | Rock |
| 2008/0184468 | A1 | 8/2008 | Stanford et al. |
| 2008/0195018 | A1 | 8/2008 | Larson et al. |
| 2008/0294079 | A1 | 11/2008 | Sterling et al. |
| 2008/0319359 | A1 | 12/2008 | Moomiaie-Qajar et al. |
| 2009/0130391 | A1 | 5/2009 | Taya |
| 2009/0234265 | A1 | 9/2009 | Reid, Jr. et al. |
| 2010/0056966 | A1* | 3/2010 | Toth ................... A61H 23/0254 601/134 |
| 2010/0197184 | A1 | 8/2010 | Browne et al. |
| 2011/0231986 | A1 | 9/2011 | Waldie et al. |
| 2011/0274903 | A1 | 11/2011 | Stuart et al. |
| 2012/0238914 | A1 | 9/2012 | Goldfield et al. |
| 2013/0019374 | A1 | 1/2013 | Schwartz |
| 2014/0081187 | A1 | 3/2014 | Wyatt et al. |
| 2015/0065930 | A1* | 3/2015 | Wyatt ................... A61H 9/0078 601/150 |
| 2015/0073319 | A1 | 3/2015 | Holschuh et al. |

FOREIGN PATENT DOCUMENTS

| | | |
|---|---|---|
| JP | 2005098241 A | 4/2005 |
| WO | WO 93/22624 | 11/1993 |
| WO | WO 2008/088197 A1 | 7/2008 |
| WO | WO 2012/154256 A1 | 11/2012 |
| WO | WO 2014/172248 A1 | 10/2014 |
| WO | WO 2016/077150 A1 | 5/2016 |

OTHER PUBLICATIONS

Ambrosino; "Novel Magnetic Sensor Based on Fiber Bragg Grating and Magnetic Shape Memory Alloys"; 1$^{st}$ International Conference on Sensing Technology; Nov. 21-23, 2005; 6 Pages.
Holschuh, et al.; "Two-spring model for active compression textiles with integrated NiTi coil actuators"; Smart Materials and Structures; Feb. 6, 2015; 15 Pages.
Holschuh, et al.; "Morphing Compression Garments for Space Medicine and Extravehicular Activity Using Active Materials"; Aerospace Medicine and Human Performance; vol. 87, No. 2; p. 84; Feb. 2016; 9 Pages.
Park, et al.; "Exoskeletal Force-Sensing End-Effectors With Embedded Optical Fiber-Bragg-Grating Sensors"; IEEE Transactions on Robotics, vol. 25, No. 6; Dec. 2009; 13 Pages.
Stirling, et al.; "Applicability of Shape Memory Alloy Wire for an Active, Soft Orthotic"; Journal of Materials Engineering and Performance; Feb. 8, 2011; 5 Pages.
Witt, et al.; "Medical Textiles With Emedded Fiber Optic Sensors for Monitoring of Respiratory Movement"; IEEE Sensors Journal; vol. 12, No. 1; Jan. 2012; 9 Pages.
Extended European Search Report dated Jun. 8, 2017 from Application No. 14843445.9; 42 Pages.
Restriction Requirement dated Jun. 1, 2017 from U.S. Appl. No. 14/482,365; 7 Pages.
Restriction Requirement dated Jun. 28, 2017 from U.S. Appl. No. 14/482,373; 6 Pages.
Response to Restriction Requirement dated Jun. 28, 2017 as filed on Jul. 17, 2017 from U.S. Appl. No. 14/482,373; 1 Page.
Extended European Search Report dated Jul. 18, 2017 from International Application No. 14844746.9; 10 Pages.
Office Action dated Sep. 27, 2017 from U.S. Appl. No. 14/482,365; 25 Pages.
Office Action dated Sep. 27, 2017 from U.S. Appl. No. 14/482,373; 41 Pages.
Tan, et al. "Effect of Annealing Temperature on the Mechanical Properties and the Spherical Indentation of NiTi Shape Memory Alloy"; Springer Science; pp. 765-772; Feb. 2013; 8 Pages.
Final Office Action dated May 3, 2018 for U.S. Appl. No. 14/482,365; 19 pages.
Final Office Action dated May 2, 2018 for U.S. Appl. No. 14/482,373; 31 pages.
"Shape memory training for smart fabrics", George K. Stylios and Taoyu Wan, School of Textiles and Design, Heriot-Watt University, Netherdale, Galashiels TD1 3HI, UK, The Institute of Measurement and Control, 2007, 16 pages.
"Stress Effects on Nitinol Phase Transformations", D. Goldstein, L. Kabacoff and J. Tydings, Journal of Metals, Mar. 1987, 6 pages.
"Research for Developing a Nitinol Linear Actuator Using a Two-Way Shape Memory Process", Teodor Socaciu, Mihai Simon, The 4$^{th}$ Editiion of the Interdisciplinarity in Engineering International Conference "Petru Maior", University of Tirgu Mures, Romania, 2009; 4 pages.
"Mechanical Analysis of Hybrid Textile Composites with NiTi Wires", Elena Villa, Sergio Arnaboldi, Ausonio Tuissi, Marco Giacomelli, and Elena Turco, Submitted Sep. 15, 2008, Revised form Dec. 10, 2008, Journal of Materials Engineering and Performance, vol. 18 (5-6) Aug. 2009; 5 pages.
Response to Restriction Requirement dated Jun. 1, 2017 as filed on Jul. 24, 2017; 1 Page.
Response to Office Action dated Sep. 27, 2017 as filed on Dec. 22, 2017; 11 Pages.
Response to Office Action dated Sep. 27, 2017 as filed on Dec. 25, 2017; 15 Pages.
PCT International Preliminary Report on Patentability dated May 26, 2017 for International Application No. PCT/US2015/059253; 6 Pages.

\* cited by examiner

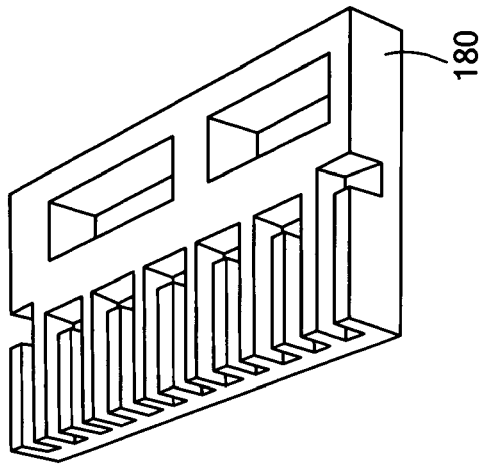
FIG. 13
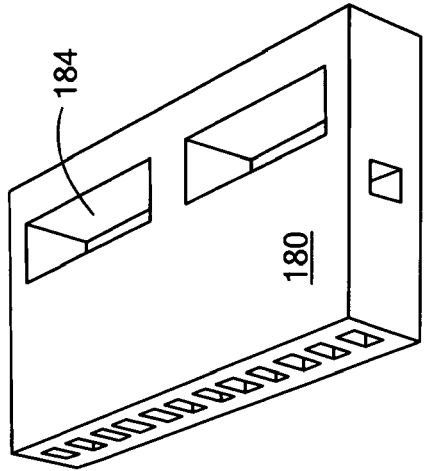
FIG. 14
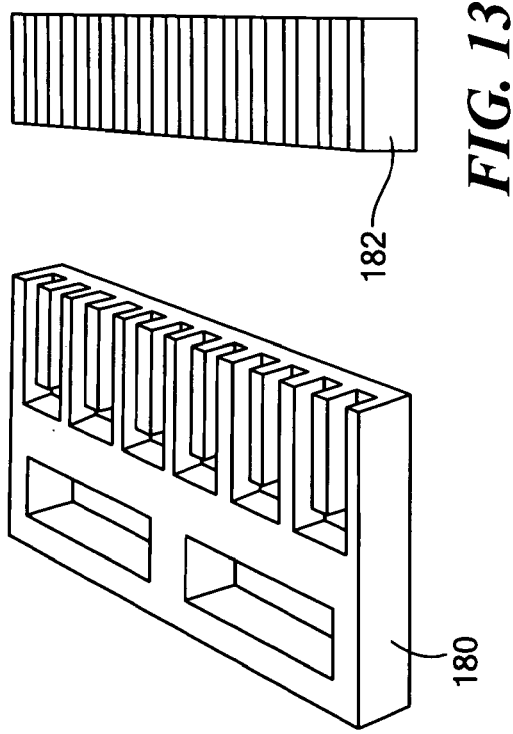
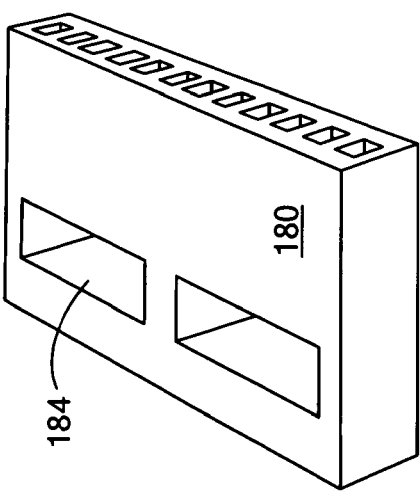

WEARABLE, SELF-LOCKING SHAPE MEMORY ALLOY (SMA) ACTUATOR CARTRIDGE

CROSS REFERENCE TO RELATED APPLICATIONS

This application is a U.S. National Stage of PCT application PCT/US2015/059253 filed in the English language on Nov. 5, 2015, and entitled "WEARABLE, SELF-LOCKING SHAPE MEMORY ALLOY (SMA) ACTUATOR CARTRIDGE," which claims the benefit under 35 U.S.C. § 119 of provisional application number 62/079,779 filed Nov. 14, 2014, which application is hereby incorporated by reference herein in its entirety.

STATEMENT REGARDING FEDERALLY SPONSORED RESEARCH

This invention was made with government support under Grant No. NNX11AM62H awarded by the National Aeronautics and Space Administration. The government has certain rights in the invention.

BACKGROUND

Compression garments are garments that provide some degree of compression to a body part of a user for a specific purpose. Compression garments might be used in a variety of different applications including, for example, medical applications, sports applications, military applications, space applications, and cosmetic applications. Some medical applications include, for example, compressive stockings to improve circulation in a wearer's legs, compression garments to be worn by diabetes sufferers, compression garments to be worn by burn victims, and post-surgical compression garments to aid in recovery after a surgical procedure. Sports-related compression garments might be used, for example, to improve the delivery of oxygen to an athlete's muscles during a sporting event. In a military or medical application, a compressive tourniquet might be used to reduce blood flow to an injured body part of a wounded person. Space applications might include, for example, compressive space suits to provide required pressurization to an astronaut's body when venturing outside of a spacecraft in space. Cosmetic applications might include girdles, corsets, and other body shapewear. Many other applications for compression garments also exist.

Compression garments are typically implemented in one of two ways. In one approach, these garments are formed of tight fitting passive materials. While lightweight, these garments are usually difficult and time-consuming to put on and take off, or provide only limited compression. In another approach, compression garments are fashioned using pneumatically-pressurized bladders. These garments can be put on and taken off relatively easily while the bladder is in a deflated state. However, such garments are typically bulky and restrict movement when inflated. There is a need for compression garments and related articles that are capable of overcoming the disadvantages of conventional compression garments.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

One aspect provides a shape memory alloy (SMA) cartridge for use in providing controllable compression. The SMA cartridge includes first and second end caps, where each of the first and second end caps are coupled to a passive material. One or more SMA coils extend between the first and second end caps. The SMA coils have a trained state and a deformed state, where the SMA coils are in the deformed state when a stimulus is provided thereto and where the SMA coils are in the trained state when the stimulus is removed therefrom. The first end cap and the second end cap include a locking mechanism to automatically lock the first and second end caps in a fixed position relative to one another when the SMA coils are contracted.

In an embodiment, the trained state of the SMA coils is a non-contracted state of the SMA coils, and the deformed state of the SMA coils is a contracted state of the SMA coils.

In an embodiment, when locked, the locking mechanism holds the cartridge in the contracted state if the stimulus is removed.

In an embodiment, the SMA cartridge includes a central spacer disposed between the first and second end caps to hold the one or more SMA coils in a fixed spaced relation to one another in the region between the end caps, where the locking mechanism locks the first and second end caps to the central spacer.

In an embodiment, the one or more SMA coils are a single SMA actuator coil. In another embodiment, the one or more SMA coils are multiple SMA actuator coils arranged in parallel.

In an embodiment, the first and second end caps each include interface structures for use in coupling each of the first and second end caps to the passive material. In some embodiments, the interface structures include attachment means configured to couple each of the first and second end caps to the passive material. In some embodiments, the interface structures include at least one lug and at least one well, the at least one lug configured to be received by a corresponding one of the at least well, thereby retaining the passive material therein. In some embodiments, the passive material is a textile material. In some embodiments, the passive material includes one or more hard or semi-hard passive structures.

In an embodiment, the locking mechanism includes at least one arm having a locking tab disposed thereon. The locking tab is configured to engage a corresponding surface of at least one of the central spacer and one of the first and second end caps when the SMA coils are in the contracted state. In an embodiment, the locking mechanism includes a release configured to permit the SMA cartridge to be unlocked from the contracted state.

In an embodiment, the SMA cartridge includes a cover enclosing the one or more SMA coils.

In an embodiment, the SMA cartridge forms an active seam of a compression garment. In some embodiments, the compression garment is one of: a bandage, a tourniquet, a mechanical counter-pressure (MCP) space suit, a compressive shirt, compressive pants, a compressive full body suit, and a compressive sleeve configured to receive a body part of interest. In some embodiments, the compression garment includes a tri-axial braid structure.

In an embodiment, the SMA coil includes a nickel and titanium (NiTi) alloy.

In an embodiment, the SMA cartridge includes at least one material, the at least one material comprising at least one of Acrylonitrile Butadiene Styrene (ABS) and a Fused Deposition Modeling (FDM) thermoplastic.

In another aspect, a compression garment is provided that includes at least one passive member for surrounding a body part of interest and at least one shape memory alloy (SMA) cartridge. The SMA cartridge is coupled to ends of the passive member for use in providing controllable compression to the body part of interest. The at least one SMA cartridge includes first and second end caps, where each of the first and second end caps are coupled to a passive material. One or more SMA coils extend between the first and second end caps. The SMA coils have a trained state and a deformed state, where the SMA coils are in the deformed state when a stimulus is provided thereto and where the SMA coils are in the trained state when the stimulus is removed therefrom. The first end cap and the second end cap include a locking mechanism to automatically lock the first and second end caps in a fixed position relative to one another when the SMA coils are contracted.

In another aspect, a method of making a shape memory alloy (SMA) cartridge is provided. The SMA cartridge provides controllable compression. The SMA cartridge is coupled to ends of the passive member for use in providing controllable compression to the body part of interest. The at least one SMA cartridge includes first and second end caps, where each of the first and second end caps are coupled to a passive material. One or more SMA coils extend between the first and second end caps. The SMA coils have a trained state and a deformed state, where the SMA coils are in the deformed state when a stimulus is provided thereto and where the SMA coils are in the trained state when the stimulus is removed therefrom. The first end cap and the second end cap include a locking mechanism to automatically lock the first and second end caps in a fixed position relative to one another when the SMA coils are contracted. The method includes generating the first and second end caps using at least one material. The first and second end caps have at least one cavity configured to receive the one or more SMA coils. At a predetermined point of the generating step, the generating of the first and second end caps is paused. While paused, the one or more SMA coils are interlacing into the at least one cavity of each of the first and second end caps. The generating step is then resumed and completed.

In an embodiment, the step of generating is performed by three-dimensional (3D) printing.

In an embodiment, the at least one material is at least one of Acrylonitrile Butadiene Styrene (ABS) and a Fused Deposition Modeling (FDM) thermoplastic.

In an embodiment, the one or more SMA coils are encased in the at least one material.

BRIEF DESCRIPTION OF THE DRAWING FIGURES

Other aspects, features, and advantages of the claimed invention will become more fully apparent from the following detailed description, the appended claims, and the accompanying drawings in which like reference numerals identify similar or identical elements. Reference numerals that are introduced in the specification in association with a drawing figure may be repeated in one or more subsequent figures without additional description in the specification in order to provide context for other features.

FIGS. 13 and 14 are diagrams of illustrative end caps and an illustrative central spacer that might be used in a single-plastic cartridge at a pre-completion stage and a completion stage, respectively, in accordance with described embodiments;

FIGS. 24 and 25 are diagrams of another illustrative SMA actuator cartridge with a locking mechanism and corresponding seam structure in accordance with described embodiments;

DETAILED DESCRIPTION

Figure 1:
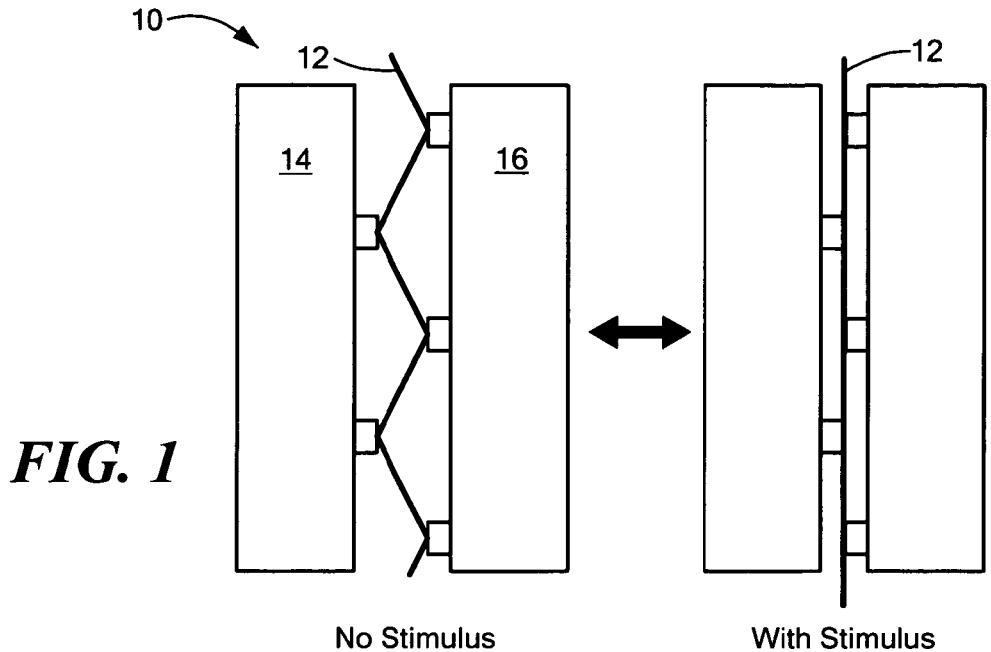
FIG. 1 is a diagram of an illustrative active seam structure of a compression garment in accordance with described embodiments.

Described embodiments provide shape memory alloy (SMA) cartridges and related structures that might be used in compression garments and other compression-related structures to provide controllable compression. The described cartridges are capable of being implemented in a low profile, lightweight manner. The described cartridges might include, for example, a plurality of SMA coil segments extending between first and second end caps. One or more central spacing units might be provided between the end caps to maintain separation between the SMA coil segments. The coil segments might all be part of the same SMA actuator (e.g., looped back and forth) or the coil segments might be part of multiple different SMA actuators. In some implementations, the SMA coil segments might be held together as closely as possible by the end caps and central spacer to achieve a maximum number of coil segments (and a corresponding maximum generated forces and pressures) within a given area. A locking mechanism might automatically lock the end caps to the central spacer upon contraction of the SMA coil segments so that a contracted state is maintained without continuous application of a corresponding stimulus (e.g., heat, electrical control signal, etc.) to the cartridge. Structures might also be provided for providing an interface between the cartridge and passive textile materials within a corresponding compression garment or other structure (e.g., snaps, buttons, etc.). The cartridges might be used in a wide variety of different compression related applications. The cartridges are particularly well suited for use in systems that require a sustained pulling force/tension/displacement without the need for continuously applied power.

Techniques, concepts, and systems described herein relate to compression garments made from a combination of traditional passive textile materials and/or semi-rigid support structures and one or more SMA actuators. Various techniques for forming and using such materials are described herein. In some embodiments, SMA actuators formed from coiled SMA wire materials are used within the SMA enhanced textile materials. Such coiled actuators are capable of providing controllable forces and shape change attributes necessary for supporting compression for a large number of different compression garment applications. Other forms of SMA actuators might alternatively be used.

As used herein, the term "compression garment" is a garment that is designed to provide compression to a body part of a user for a specific purpose, other than holding the garment on the wearer. Thus, a conventional pair of socks might provide some level of compression to a wearer's legs so that they do not fall down, but these are not considered compression garments. A compression stocking worn by a diabetic to improve circulation, however, is considered a compression garment for purposes of this disclosure. The word "garment" is used herein in a broad sense to encompass anything that may be worn on a body, regardless of size or location, and is not limited to items that are normally considered clothing. Thus, structures like bandages, tourniquets, and the like are considered herein to be garments.

SMAs are a category of metal alloys that demonstrate a shape memory effect, which is the ability to return from a deformed state to a "remembered" state when exposed to a specific stimulus. This occurs as a result of a diffusionless solid-to-solid transformation between the alloy's austenitic and martensitic phases that is triggered by an external stimulus. Stimuli can take several forms, including externally applied stress, heat, or magnetic fields, among others. Shape memory alloys also demonstrate super-elasticity, which is the ability to recover fully their strain throughout a loading and unloading cycle, though hysteresis-based energy losses can occur. The deformations that can be recovered through the shape memory effect are significant. For example, an SMA wire that is deformed from its original configuration, then exposed to heat, causes the SMA wire to return to its original, un-deformed "memory" shape. Both the memory shape and the activation temperature threshold of an SMA wire can be tailored for custom applications. The memory shape can be set by annealing the alloy while fixed in the desired shape. The activation temperature can be set by, for example, modifying the alloy mixture.

The shape memory and elastic properties of SMAs have proven useful in a wide variety of applications, ranging from robotic actuators and prostheses to bridge restraints, valves, deformable glasses frames, biomedical devices, and wearable garments. The memory effect has been demonstrated in several alloy types, though the most common and commercially available alloy produced is NiTi (approximately 55% Nickel and 45% Titanium), under brands such as Nitinol® and Flexinol®. Some other alloys include, for example, silver-cadmium (AgCd), copper-aluminum-nickel (CuAlNi), manganese copper (MnCu), and others. Such alloys can be purchased in wire, tube, strip, or sheet form in varying thicknesses and diameters, and their deformation recovery capabilities scale with element size. Although generally described herein as employing NiTi material, described embodiments might employ other SMA materials in connection with the techniques, structures, and systems described herein.

SMAs are widely available and relatively inexpensive. With proper design and manufacturing, SMAs can produce large forces, recover from large deformations, and can be integrated into textiles. A limitation of SMAs, however, is the small magnitude of recoverable strain. For example, current SMAs demonstrate strains that peak in the single-digit percentage range. This poses challenges for applications that require large stroke lengths. In a controllable compression garment, for example, compression requires constriction of a garment surrounding a body member. This is most easily achieved through length-wise (i.e., circumferential) constriction of a garment's individual active SMA elements. Based on the strain of SMAs alone, for example, it would be difficult to produce the counter-pressure (e.g., 30 kPa) required for a mechanical counter-pressure (MCP) space suit compression garment while also providing for significant shape changing capability (to support donning and doffing, for example). However, SMAs can produce the required compression with significant active strains due to their superelasticity and large deformation abilities.

As described herein, various embodiments provide controllable compression garments that are formed from textiles that include SMAs. The SMAs might be implemented as SMA actuators that are incorporated with more conventional passive textile materials. In addition to the selection of active SMA materials, a garment architecture must also be selected in which the active materials can be embedded. The architecture selection involves consideration of macro-textile physics properties as well as production methodologies for textile subcomponents (e.g., fibers and threads) as applied to active materials. The architecture must be capable of transforming SMAs from generic actuators to a form appropriate for integration into a wearable, controllable garment.

Hybrid garment architectures are described herein that can be used with SMA actuators to produce compression garments for use in different compression applications. These hybrid architectures include, for example, (1) an architecture that uses an active seam structure that includes SMA actuators; (2) an architecture that uses a tri-axial braid structure with SMA actuators; (3) an architecture that uses an active tourniquet structure with SMA actuators; (4) an architecture that uses two or more hard or semi-hard passive structures that are coupled together using SMA actuators;

and (5) an architecture that uses one hard or semi-hard passive structure that is coupled to a soft, flexible passive structure using SMA actuators. It should be understood that the above-listed architectures represent examples of some exemplary hybrid architectures that may be used in embodiments. Many other hybrid architectures may alternatively be used.

As described, in various embodiments, SMA coil actuators are used within hybrid garment architectures. Coil actuators are capable of providing both high force and large displacement. An SMA coil actuator can be initially trained, for example, as a tightly wound shorter structure. This can be done by, for example, subjecting the coil to high heat. The actuator might then be deformed by lengthening the coil longitudinally. A stimulus can then be applied (e.g., a voltage, an increased temperature, etc.) that will cause the coil to return to its trained dimension. After the stimulus is removed, the coil actuator can be deformed again and the process repeated.

In general, the force that is generated by providing a stimulus to a deformed SMA coil actuator is maximized as the "spring index" C of the coil is minimized. The spring index might be defined as the ratio of the diameter D of the coil to the diameter d of the SMA wire. Traditionally, the minimum manufacturing limit for the spring index C of a coil is approximately 3. In some embodiments, coil actuators are used that are as close to the minimum spring index as possible. For example, in one embodiment, an SMA wire having a diameter of 305 µm (e.g., 305 µm Flexinol® wire) is formed into a coil having an average coil diameter $D_{avg}$ of 940 µm, providing a spring index of 3.08, and providing a balance between the thickness of the wire and the low-profile nature of the coil. Coils having other diameters and spring indexes might be used in other embodiments. It is possible to use SMA coil actuators with the hybrid architectures described herein, although other actuator types might alternatively be used.

FIG. 1 shows an illustrative active seam structure 10 for use in a compression garment. As shown, the active seam includes SMA coil actuator 12 that couples together first end 14 and second end 16 of a passive textile to form a garment (not shown in FIG. 1). The passive textile might be wrapped about a body part of a wearer. With no stimulus applied, SMA coil actuator 12 might be deformed into a position that opens the seam, easing donning and doffing of the garment. With stimulus, SMA coil actuator 12 might return to a trained (i.e., contracted) state that closes the seam and compresses the corresponding body part. When the stimulus is again removed, the seam might again be opened by deforming SMA coil actuator 12 into the open position. Although shown in FIG. 1 as having SMA coil actuator 12 open the seam when no stimulus is applied and close the seam when stimulus is applied, in other embodiments, the application of stimulus might be reversed such that when no stimulus is applied, SMA coil actuator 12 closes the seam, and when stimulus is applied, SMA coil actuator 12 opens the seam.

Figure 2:
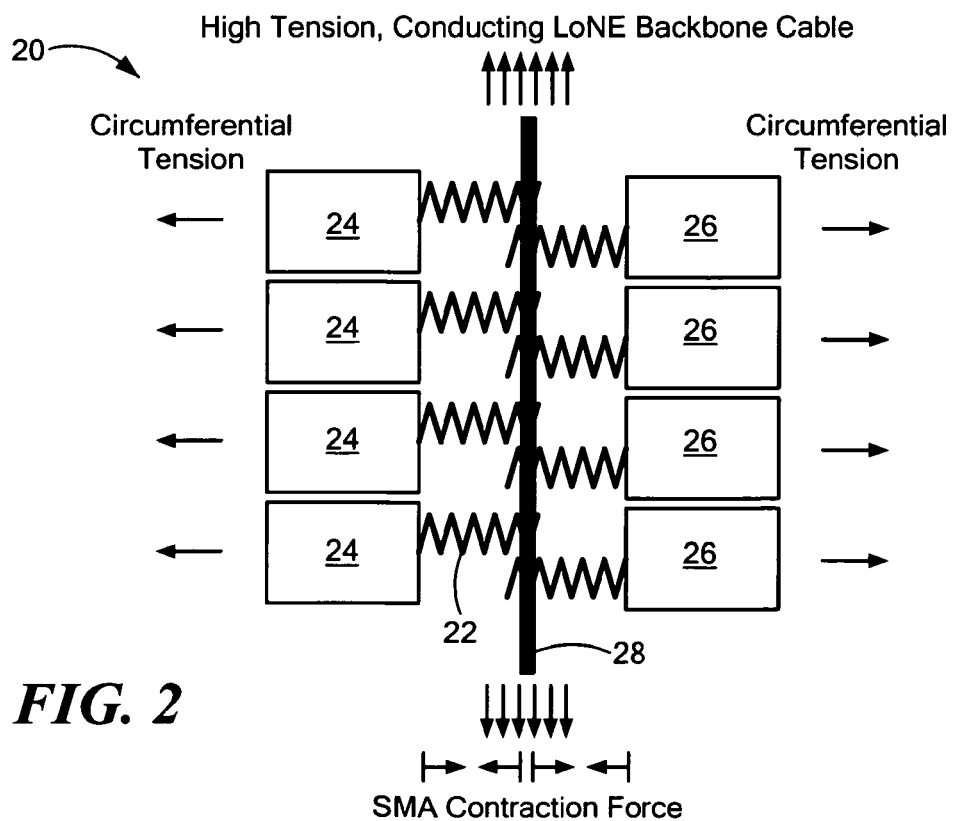
FIG. 2 is a diagram of another illustrative active seam structure of a compression garment in accordance with described embodiments.

FIG. 2 shows illustrative active seam structure 20 that might be used in a compression garment. As shown in FIG. 2, a number of SMA coil actuators 22 are coupled between first end 24 and second end 26 of a circumferentially aligned passive textile member (not shown in FIG. 2). SMA coil actuators 22 might each be coupled between a respective one of the ends 24 and 26 of the passive member and a high tension or rigid backbone 28. Alternatively, one or more (or all) of actuators 22 might be directly coupled between the two ends 24 and 26 of the passive member. Backbone 28 (which in one embodiment could be implemented as a high-tension cable) runs along a line of non-extension (LoNE) associated with the wearer. Illustrative techniques for identifying LoNEs of a wearer for designing a garment are described in related U.S. patent application Ser. No. 13/274,992 filed Oct. 17, 2011, and Ser. No. 14/837,455 filed Aug. 27, 2015, and International Patent Application No. PCT/US2015/053978 filed Oct. 5, 2015, which are commonly owned with the present application, and the teachings of which are hereby incorporated by reference herein.

Backbone 28 might beneficially be formed from a conductive material or contain conductive pathways to allow a control signal to be applied to actuators 22 to cause them to transition between a trained state and a deformed state, thus allowing compression to be applied to a body part of the wearer and facilitating donning and doffing of the garment. Other active seam configurations might alternatively be used within a compression garment in other implementations. As shown in FIG. 2, the SMA contraction force is generally orthogonal to backbone 28, and is exerted to close the seam.

In some embodiments, SMA coil actuators are used in conjunction with passive braid structures within compression garments. A braid is a textile superstructure composed of individual fibers, yarns, or fabric elements that are "mutually intertwined in tubular form". Several different braiding arrangements (e.g., diamond, regular, Hercules, etc.), axial configurations (e.g., biaxial, triaxial), fiber diameters and porosities, and intertwining angles (e.g., from 10-80 degrees) are possible. Because of their unique architecture, braided structures have the ability to change both length and diameter, as the fiber elements are free to rotate angularly with respect to one another. For this reason, braided tubes have been utilized in many actuation and morphing engineering structures, for example including pneumatic artificial muscles, expandable tubing sheaths, and in-vitro stents.

Figure 3:
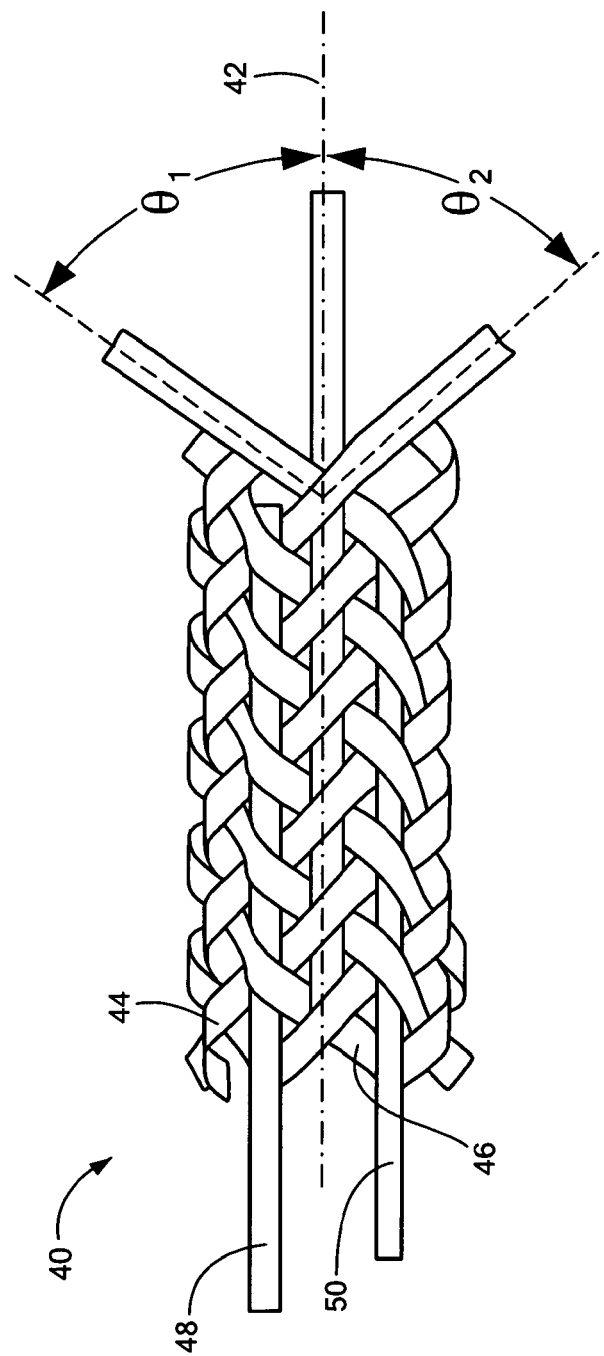
FIG. 3 is a diagram of an illustrative tri-axial braid structure that might incorporate one or more Shape Memory Alloy (SMA) actuator structures in accordance with described embodiments.

FIG. 3 shows an illustrative tri-axial braid structure 40 that might incorporate one or more SMA actuator structures. As shown, tri-axial braid structure 40 might include positive bias yarn 44 and negative bias yarn 46 that are intertwined at angles to one another relative to the longitudinal dimension 42 of the braid (e.g., angles $\theta_1$ and $\theta_2$). In one approach, positive bias yarn 44 and negative bias yarn 46 of braid 40 are formed of a passive material. Tri-axial braid 40 might also include one or more zero degree yarns (e.g., zero degree yarns 48 and 50) and one or more circumferential yarns (not shown). In some embodiments, some or all of zero degree yarns 48 and 50 and some or all of the circumferential yarns (not shown) of tri-axial braid structure 40 are implemented using SMA actuators or wires. In such an approach, the circumferential actuators are used to, for example, contract the braid structure about a wearer's body part to apply compression thereto, which will lengthen (and compress) the braid. The stimulus may later be removed from the circumferential actuators and applied to the zero degree actuators. These actuators then contract, thereby shortening (and opening) the braid. The open braid is conducive for easy donning and doffing of the garment. In some implementations, only circumferential actuators are used. Using this approach, after a stimulus is removed from the circumferential actuators, human force may be used to open the braid.

Figure 4:
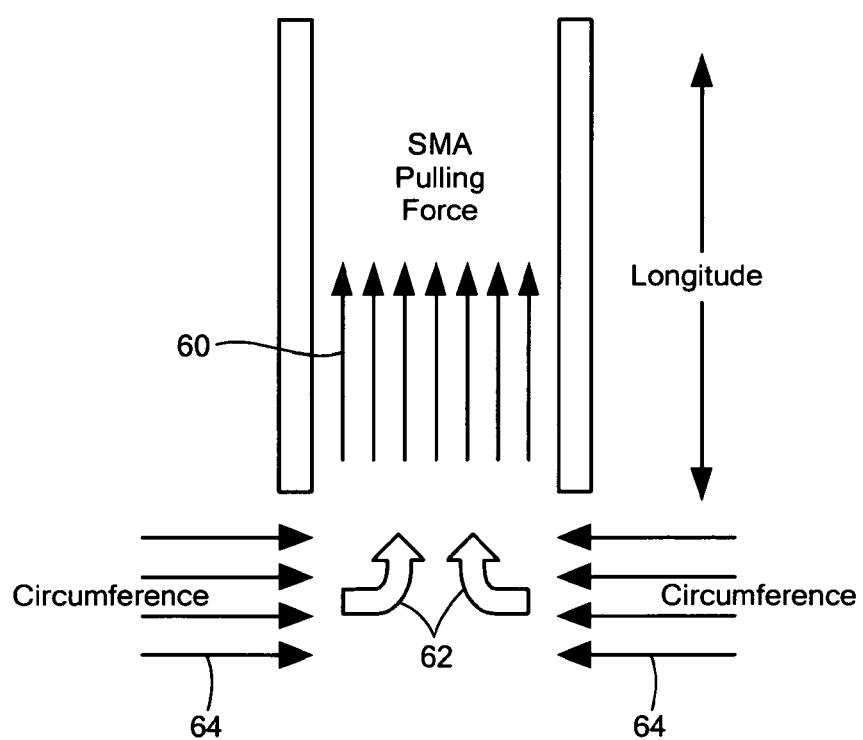
FIG. 4 is a diagram of an illustrative technique for operating an active tourniquet in accordance with described embodiments.

FIG. 4 shows a technique to provide a tourniquet incorporating one or more SMA actuators in accordance with described embodiments. The technique allows compression to be applied to a body part of a wearer via a circumferential passive textile element using forces generated by SMA actuators 60 that are oriented in a non-circumferential (e.g., longitudinal) direction. Using this approach, much longer SMA actuators (e.g., coil actuators) might be used and greater compressive forces can be generated since the actuators are not limited by the dimensions of the circumferential compressive element. As shown, to apply compression, a stimulus is applied to SMA actuators 60 to generate longitudinal forces ("SMA pulling force"). Direction changing structures 62 can be used to change the direction of the generated forces to the circumferential direction 64. These circumferential forces then act to tighten the circumferential passive member (e.g., a cuff, etc.) in a manner that compresses the body part of interest.

Figure 5:
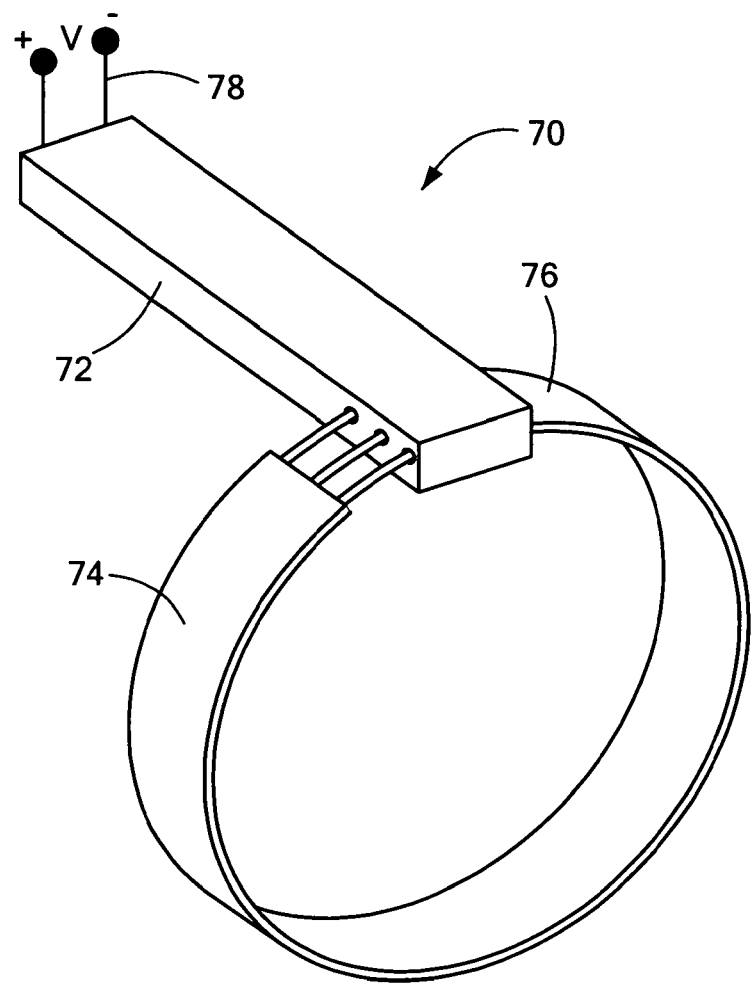
FIGS. 5 and 6 are diagrams of an illustrative tourniquet structure that might be used to carry out the technique shown in FIG. 4 in accordance with described embodiments.
Figure 6:
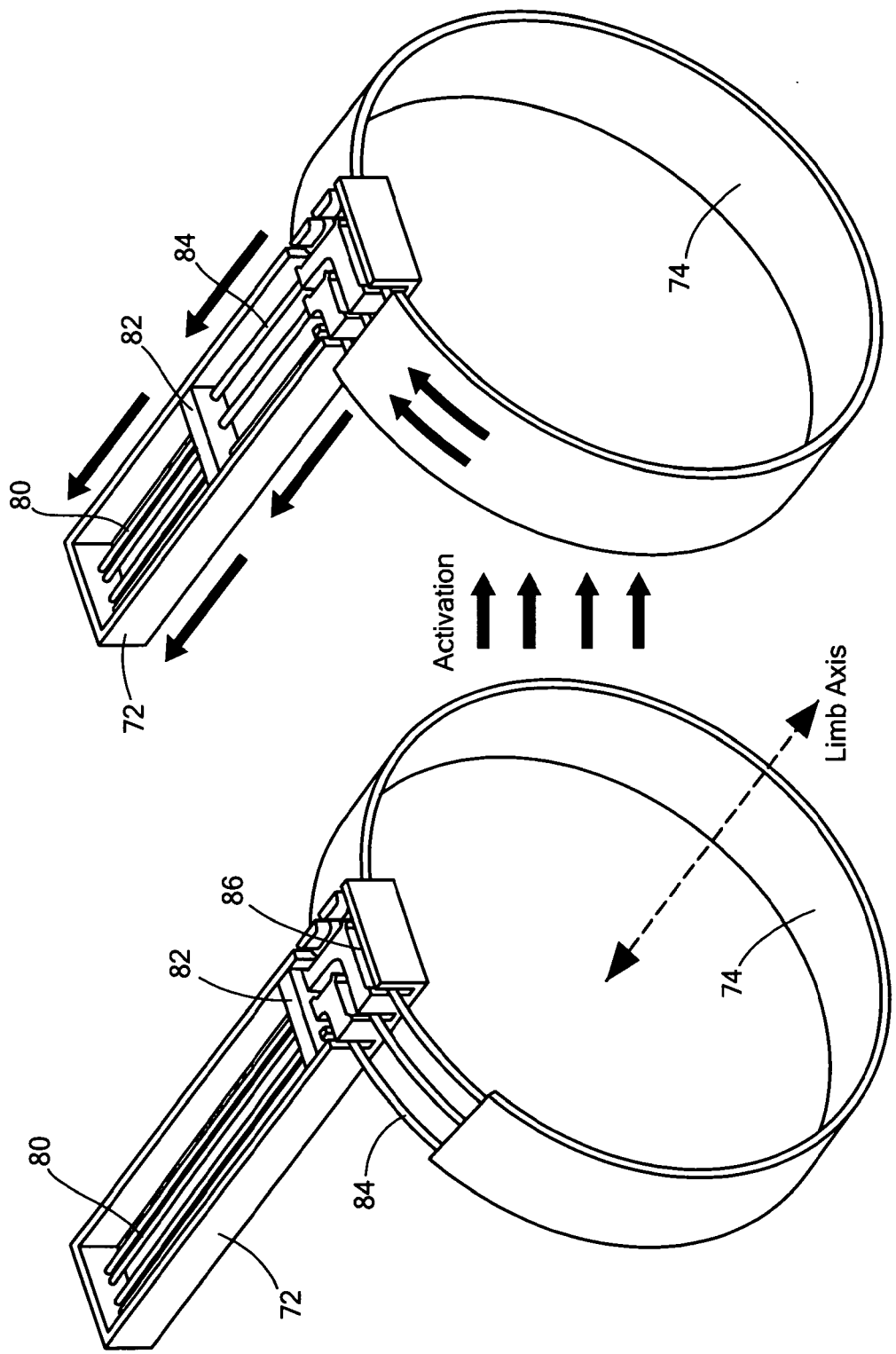

FIGS. 5 and 6 show illustrative tourniquet structure 70 that might be used to carry out the technique shown in FIG. 4. As shown in FIG. 5, base unit 72 might be provided that houses a number of SMA actuators (not shown). Compressive cuff 74 is made out of a passive material and is secured to base unit 72 at one end thereof (e.g., end 76). Base unit 72 might also include one or more electrical terminals 78 for the application of a voltage or other stimulus signal to apply compression once compressive cuff 74 is fit around a body part. When the stimulus is applied, wires or other structures within base unit 72 cause compressive cuff 74 to tighten around the body part in a desired manner.

FIG. 6 shows operation of tourniquet structure 70 of FIG. 5 in accordance with described embodiments. As shown in FIG. 6, multiple SMA coil actuators 80 are disposed within base unit 72, with each of SMA coil actuators 80 coupled between an end wall of base unit 72 and moveable block 82. Wires 84 are coupled to an opposite side of moveable block 82. As shown, wires 84 extend into channel regions 86 within base unit 72, and channel regions 86 are employed to change the direction of wires 84 and the corresponding forces associated therewith. Wires 84 emerge from a side of base unit 72 where they are coupled to compressive cuff 74 for applying pressure to a body part of interest. A lid (not shown) might be provided to enclose (fully or partially) base unit 72 to protect SMA actuators 80, wires 84 and other structures therein. Although coil based actuators are used in the illustrated embodiments, it should be appreciated that other actuators types might be used in other implementations. Other structures for changing the direction of the actuator-generated forces might also be used.

On the left side of FIG. 6, the tourniquet is shown with SMA coil actuators 80 de-twinned for donning and doffing of the tourniquet. As illustrated, moveable block 82 is located at an end of an internal cavity of base unit 72 and wires 84 extend a certain distance outside base unit 72. On the right side of FIG. 6, the tourniquet is shown with stimulus applied to SMA coil actuators 80. The stimulus causes SMA actuators 80 to contract, which pulls moveable block 82 toward an opposite end of the internal cavity of base unit 72. This action draws wires 84 into base unit 72, thus tightening compressive cuff 74 around a body part within the cuff (if any). When the stimulus is subsequently removed, a user can manually pull open the cuff for removal from the body part.

Although illustrated with four SMA actuators 80, it should be appreciated that any number of actuators might be used in different implementations. The number of wires 84 that are coupled to the compressive cuff 74 does not have to match the number of actuators 80. In some embodiments, moveable block 82 is not used. For example, wires 84 that emerge from base unit 72 might be wires associated with actuators 80 themselves. Further, wires 84 that emerge from base unit 72 might emerge on one or both opposing sides of the structure (attaching to one or both ends of compressive cuff 74). One or more compressive cuffs 74 might be aligned along the length of base unit 72, with one or more moveable block/SMA actuator subsystems operating within base unit 72 similarly as described above.

Figure 7:
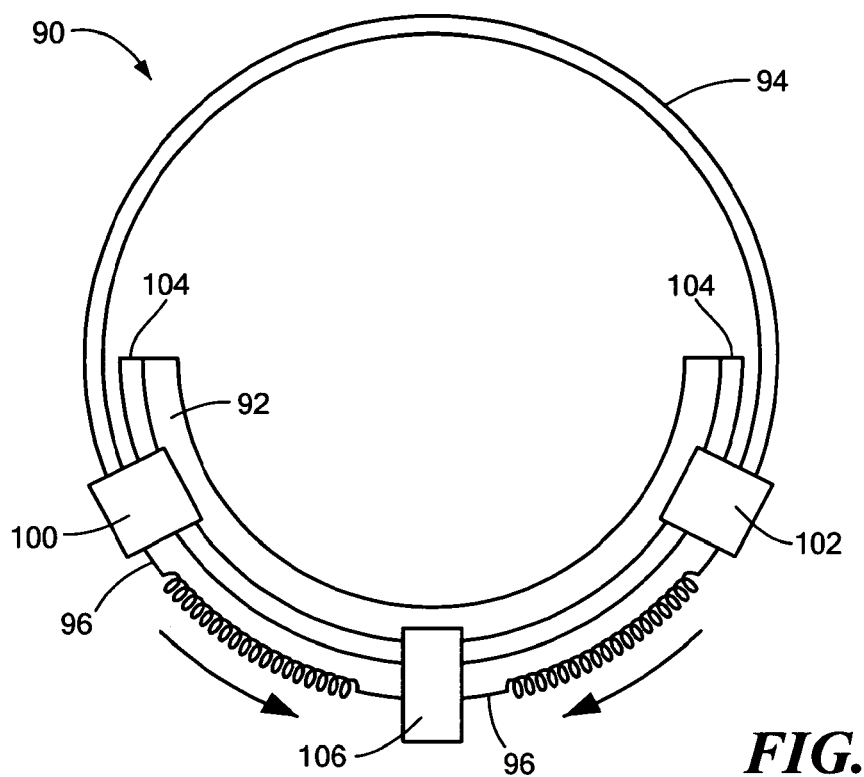
FIG. 7 is a diagram of an illustrative compression garment architecture that uses a rigid or semi-rigid passive member and a flexible passive member to surround and compress a body part in accordance with described embodiments.

FIG. 7 shows an illustrative compression garment architecture 90 that uses a rigid (or semi-rigid) passive member 92 along with a flexible passive member 94 to surround and compress a body part in accordance with an embodiment. One or more SMA actuators 96 are used to provide the forces necessary to move flexible member 94 with respect to rigid member 92 to provide compression to a body part inside the structure. As shown, in some embodiments, one or more moveable blocks (shown as moveable blocks 100 and 102) are provided that move along rails 104 associated with rigid passive member 92. Flexible passive member 94 might be coupled to moveable blocks 100 and 102 at one or both ends thereof. One or more SMA actuators 96 might be coupled between each movable block 100 and 102 and a corresponding stationary structure 106 that is fixed to rigid passive member 92. Any number of actuators 96 might be used and, in some embodiments, parallel arrangements of many actuators are used.

When a stimulus is applied, SMA actuators 96 contract, thereby pulling flexible passive member 94 into or over rigid member 92 (or stretching flexible passive member 94 towards and adjacent to rigid member 92) and applying compression to a body part located inside members 92 and 94. In one embodiment, one end of flexible passive member 94 is fixed to rigid passive member 92 and the other end is moveable. In the embodiment shown in FIG. 7, both ends of flexible passive member 94 are moveable with respect to rigid member 92.

Figure 8:
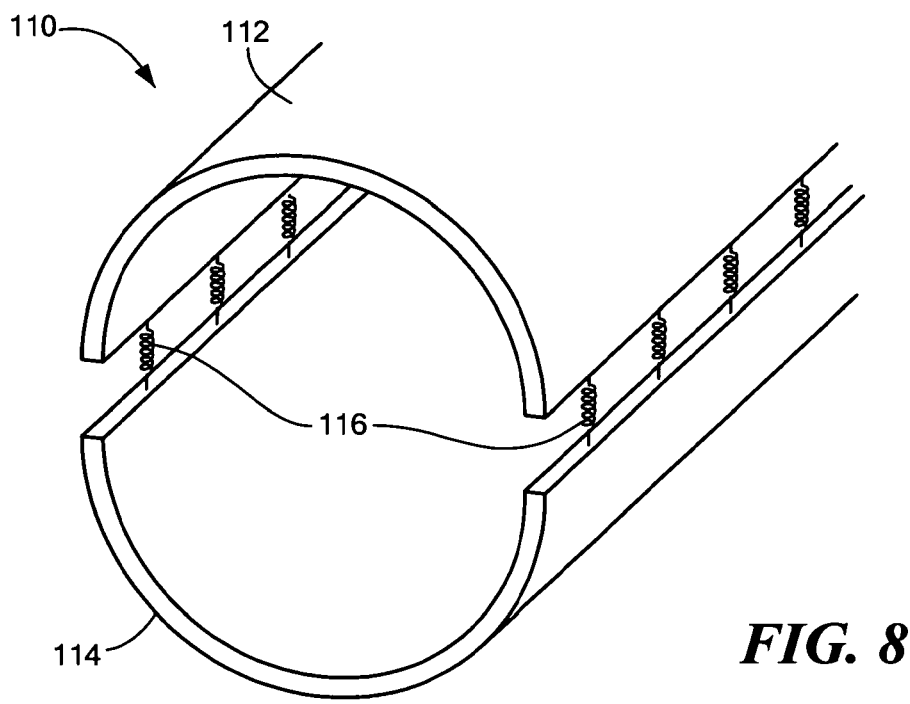
FIG. 8 is a diagram of an illustrative compression garment architecture that uses two or more rigid or semi-rigid passive members that are interconnected using SMA actuators to provide compression in accordance with described embodiments.

FIG. 8 shows an illustrative compression garment architecture 110 that uses two rigid (or semi-rigid) passive members 112 and 114 that are interconnected using SMA actuators 116 to provide compression. As shown, when no stimulus is applied, passive members 112 and 114 can be pulled apart to allow easy donning and doffing of the garment. When stimulus is applied, actuators 116 pull the two passive members 112 and 114 together, thus applying compression to a body part of interest. When the stimulus is removed, passive members 112 and 114 can again be pulled apart. Although not shown, it should be appreciated that mechanical guides may be provided to control the opening and closing of the garment. Similarly, in some implementations, protection structures may be provided to protect actuators 116 from damage. Further, more than two passive members might be used. Any number of actuators 116 might be used including, in some embodiments, a large number of parallel actuators. In at least one embodiment, SMA actuators 116 are only used on one seam between the two passive members 112 and 114 (e.g., the seam on the right side in FIG. 8). The other seam (e.g., the seam on the left side in FIG. 8) might use passive, flexible materials to provide coupling.

Although not shown in all the figures, it should be appreciated that structures will typically be provided to allow control signals to be applied to the various SMA actuators. In most cases, the control signals will be electrical signals and the structures that are provided to apply the signals will be terminals, contacts, or leads and corresponding conductor lines that are conductively coupled to each of the actuators to be used. In some embodiments, each individual actuator may be separately controlled. In others, multiple actuators may be coupled together, either in series, in parallel, or some serial/parallel combination, for the purpose of applying control signals. Any technique may be used for providing control signals to the actuators of a garment in various embodiments.

Delivery of control signals can be accomplished using electrified conductive fibers integrated as necessary into the respective textile structures. In some embodiments, non-electrified (thermal) activation of the active structures through conductive heating may be used. In some implementations, for example, simple contact with the wearer may prove sufficient for activation (if the shape changing elements have sufficiently low activation temperatures) requiring no external power or thermal source. In other implementations, direct contact of actuators with an adjacent thermal element may be used to impart thermal energy for activation. The force response of a given SMA coil actuator, when held at a fixed displacement, scales approximately linearly with temperature (and therefore with applied voltage) up to the final activation temperature of the specific material used (and this temperature is modifiable based on the specific shape change material properties and annealing method used in its manufacturing). This enables precision force and displacement control of the system through the applied signals, with enables a specialized compression response that can be tailored for a given application.

As described herein, active compressive garments might perform compression when a stimulus is applied, and that open, or can be opened, through deformation of the actuators when the stimulus is removed. In some embodiments, however, the compressive state might occur when the stimulus is not applied where the stimulus is used to remove the compression and open the garment. This may be desired, for example, in an application where the compression state is a fail-safe state. For example, in a space application, a space suit typically must maintain a pressurized condition while an astronaut is outside a space vehicle. If a power source fails in such a scenario, the space suit must remain pressurized. Thus, the suit might preferably be configured to provide compression with no signal applied and to relieve compression when a signal is subsequently applied (e.g., when the astronaut returns to the ship and wants to remove the suit).

Figure 9:
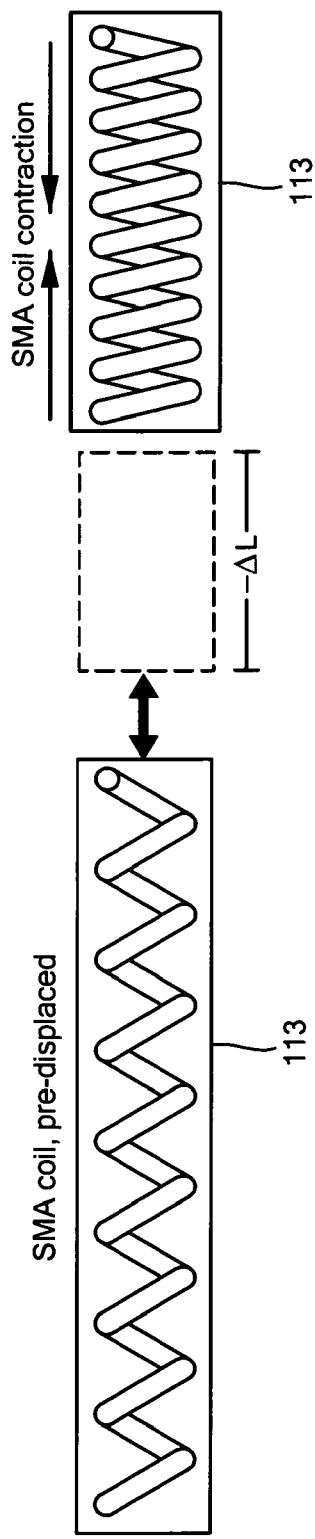
FIG. 9 is a diagram of an illustrative SMA coil actuator encapsulated within an elastomeric material in accordance with described embodiments.

In some embodiments, SMA coil actuators are encapsulated within an elastomeric material before being placed within one or more compression garments or fabrics, forming a composite fiber, such as shown in FIG. 9. As shown in FIG. 9, elastomeric material 113 provides electrical and/or thermal insulation for the actuator, for example, to prevent shorting of the actuator to other actuators and/or other conductive structures, or to provide thermal insulation. Elastomeric material 113 might also provide physical protection to the coil from other potential sources of harm in a corresponding system, and may provide a cylindrical (rather than helical) form factor, which can be advantageous in a textile configuration. Elastomeric material 113 is selected so as to be pliant enough to allow the SMA coil actuator to fully compress and expand along with the SMA actuator. Thus, elastomeric material 113 is selected to be a material that is capable of transitioning between an original shape and a deformed shape (e.g., based on the application of stimulus to the SMA actuator).

Different elastomeric materials might be used to achieve the aforementioned shielding of elastomeric material 113 in various described embodiments. In one embodiment, de-twinned (i.e., extended) coil actuators are cast in cylindrical form (of diameter equal to, or greater than, the coil diameter) in soft silicone resin (e.g., Shore 10A-30A hardness) using a precisely machined Teflon® cast. Such an actuator has been shown to still achieve activation (i.e., the resin is sufficiently soft to enable contraction without damaging the composite matrix), and it is believed that such actuators will be capable of achieving a repeatable two-way response. Other similar embodiments are possible using a variety of materials, including foam rubber resin, neoprene resin, and other sufficiently soft, insulating elastomers.

In some embodiments described herein, SMA actuators formed from coiled SMA wire materials are used within compression garments. NiTi coils, for example, can achieve displacements that are orders of magnitude greater (>100%) than those of typical axially aligned SMA wires. The combination of high forces, large displacements, simple activation mechanism, low mass, compact form factor and fiber-like aspect ratio make NiTi SMA coil structures well suited for inclusion in an active compression textile. To fabricate such coils, a coil winding process is used.

Figure 10:
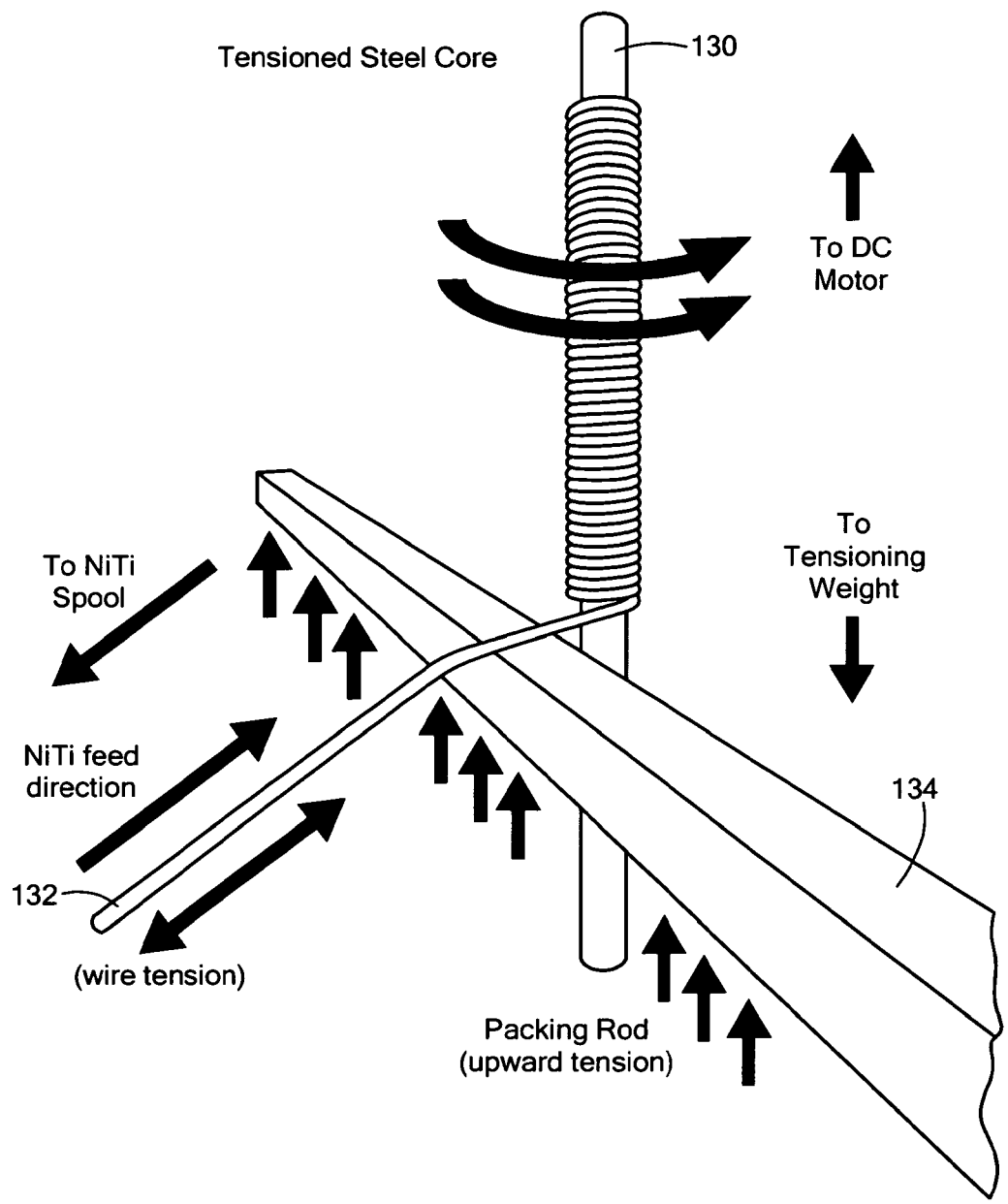
FIG. 10 is a diagram of an illustrative SMA coil fabrication process in accordance with described embodiments.

One such process that is capable of producing low spring index SMA coil actuators is shown in FIG. 10. As shown, the winding may be accomplished by hanging steel core 130 under tension from a variable speed DC motor, and progressively feeding NiTi wire 132 along the length of core 130 using packing rod 134 as core 130 rotates. Downward tension is induced in NiTi wire 132, and upward tension is provided by packing rod 134 at the point of winding to ensure tight packing density and consistent pitch angle. In one implementation, a 305 μm (0.012") NiTi Flexinol® muscle wire is used with a 635 μm (0.025") stainless steel core, resulting in a spring index, C, of 3.08, to repeatably produce coils with an average packing density η=0.887 (±0.02, at 95% confidence). The specific NiTi wire diameter (e.g., 305 μm) can be selected as a compromise between maximum force (and therefore maximum pressure) and coil thickness (coil outer diameter). In this case, the outer diameter (~1.25 mm) determines the bulkiness of the actuator system relative to the passive textile thickness.

Once wound at room temperature, each coil is clamped on both ends to retain its shape and annealed at 450° C. for 10 minutes to set the austenite memory state. After this, the coil is water quenched and the steel core and clamps are removed. These annealing parameters were selected as a balance between minimizing de-twinning force and minimizing permanent plastic deformation after actuation.

NiTi compression coils can be defined by several key parameters, including (1) the NiTi wire diameter d; (2) the spring diameter D, as measured by the midpoint between inner and outer diameters; (3) the number of active coils, n; (4) the solid spring length, $L_S$, defined as the length of a spring that is fully packed; (5) the free spring length, $L_0$, defined as the zero-load length of the spring which, for SMA actuators described herein is the length of the SMA actuator when fully actuated with no load; (6) the spring pitch, p, defined as the distance between adjacent coils; (7) the spring pitch angle, defined as the angle between a given coil and the local horizontal; (8) initial and final extended spring length, $L_i$ and $L_f$, defined in this case as the total extended spring length pre- and post-activation under no load; and (9) the initial and final linear displacements $\delta_i$ and $\delta_f$, defined as the difference between initial and final extended spring length and free spring length. Actuator force follows Hooke's law, and can be expressed as:

$$F = k\delta = \left(\frac{Gd^4}{8D^2\pi}\right)\delta \quad (1)$$

where G is the SMA austenite shear modulus.

Relation (1) above can be simplified by defining three non-dimensional parameters: packing density, $\eta$; actuator extensional strain, $\varepsilon$; and spring index, C. Packing density, $\eta$, is defined as the ratio of the number of active coils contained in the free spring length $L_0$ relative to the physical limit, which can be defined as the ratio of the solid spring length $L_S$ to the free spring length $L_0$ expressed as:

$$\eta = \frac{L_S}{L_o} = \frac{nd}{L_o} \quad (2)$$

Actuator extensional strain $\varepsilon$ is defined as the ratio of spring displacement $\delta$ to free spring length $L_0$. Spring index C is a universal spring parameter defied as the ratio of spring diameter D to wire diameter d, which is a measure of coil curvature. Substitution then results in relation (1) being expressed as:

$$F = \left(\frac{Gd^2}{8C^3\eta}\right)\varepsilon \quad (3)$$

Relation (3) allows actuators to be designed to meet specific performance requirements, which may include force targets, size limitations, manufacturing limitations, or desired lengths or extensional strains. For example, force may be maximized by maximizing G, d, and, and by minimizing C and. Maximum force can be achieved when an SMA spring actuator is comprised of thick diameter wire wound to the tightest spring index, and is de-twinned to the mechanical limit with the lowest possible packing density. Such a design, however, requires tradeoffs in terms of actuator size and maximum actuator stroke length (i.e., longer stroke lengths can only be achieved when spring index is increased and packing density is increased, and large diameter SMA wire translates to large coil diameter, even with a minimized spring index). Alternatively, actuator design targets can be achieved by scaling the number of actuators used if it is not possible to satisfy all constraints with a single actuator. However, increasing the number of actuators in a given system creates both a larger system footprint and greater power requirement. Therefore, specific consideration of each design variable must be given when engineering a system for a desired application.

For example, high force creation is desirable for wearable structures using SMA coil actuators. Therefore, high force generation might be prioritized over other design variables (e.g., to create maximum counter-pressure) in some implementations. The following criteria might be used to achieve maximum (or near maximum) force: (1) Maximize force by minimizing spring index C. A physical limit to the sharpness of curvature of a spring actuator exists, below which the material experiences structural damage. Actuators can be selected that match this minimum (C=3). (2) Maximize force by selecting as large a wire diameter d as is reasonable for a wearable system. While actuator force scales with the square of wire diameter (meaning that a maximum wire thickness should be used if force is to be purely maximized), this cannot be simply maximized due to design constraints associated with wearable garments (e.g., overly thick actuators that encumber the wearer). Practical constraints for wearable systems (e.g., MCP garments) dictate a garment thickness ≤5 mm. Commercial NiTi wire is available as thin as d=25 µm, and as thick as d=510 µm. Reasonably large SMA wire diameters (e.g., d=305 µm) thus might beneficially be selected for use in an MCP garment. (3) Enable large extensional strains $\varepsilon$ by selecting high packing densities $\eta$. In addition to large active forces, MCP compression suits require significant active stroke lengths to accommodate donning and doffing prior to active compression. These requirements cannot both be maximized, in terms of selecting appropriate $\eta$ and $\varepsilon$ values since increased force calls for minimizing $\eta$, while increased stroke length calls for maximizing $\eta$ to increase $\varepsilon$. Consequently, maximum $\eta$ for a fixed C might be selected to provide as much extensional strain $\varepsilon$ as possible.

One challenge in developing active compression garments using SMA actuators is to design a packaging solution for the SMA actuators themselves. While individual actuators have been shown to produce sizable forces when a voltage is applied, the magnitude of force required for some compression garment applications (e.g., MCP space suits, etc.) may only be achieved when several actuators are aligned in parallel. In such a configuration, it is advantageous to minimize the space between actuators (i.e., to pack them as close together as possible) because this maximizes the total force produced per unit width. However, the actuators have a physical limit in how closely spaced they can be, for example to prevent actuators from short-circuiting to each other. Further, the actuators must be sufficiently fixed in place to prevent structural failure (e.g., an actuator breaking free from the garment or passive fabric) during operation (especially at high tension/pressure levels).

In some implementations, SMA actuators are packaged as a cartridge-style SMA actuator structure for use in active compression garments and other applications. An SMA actuator cartridge might include, for example, a self-contained actuator assembly that includes multiple parallel SMA coil segments that may be activated in unison. An SMA actuator cartridge might also include structures that are easily mated to passive textile portions of a compression garment.

Figure 11:
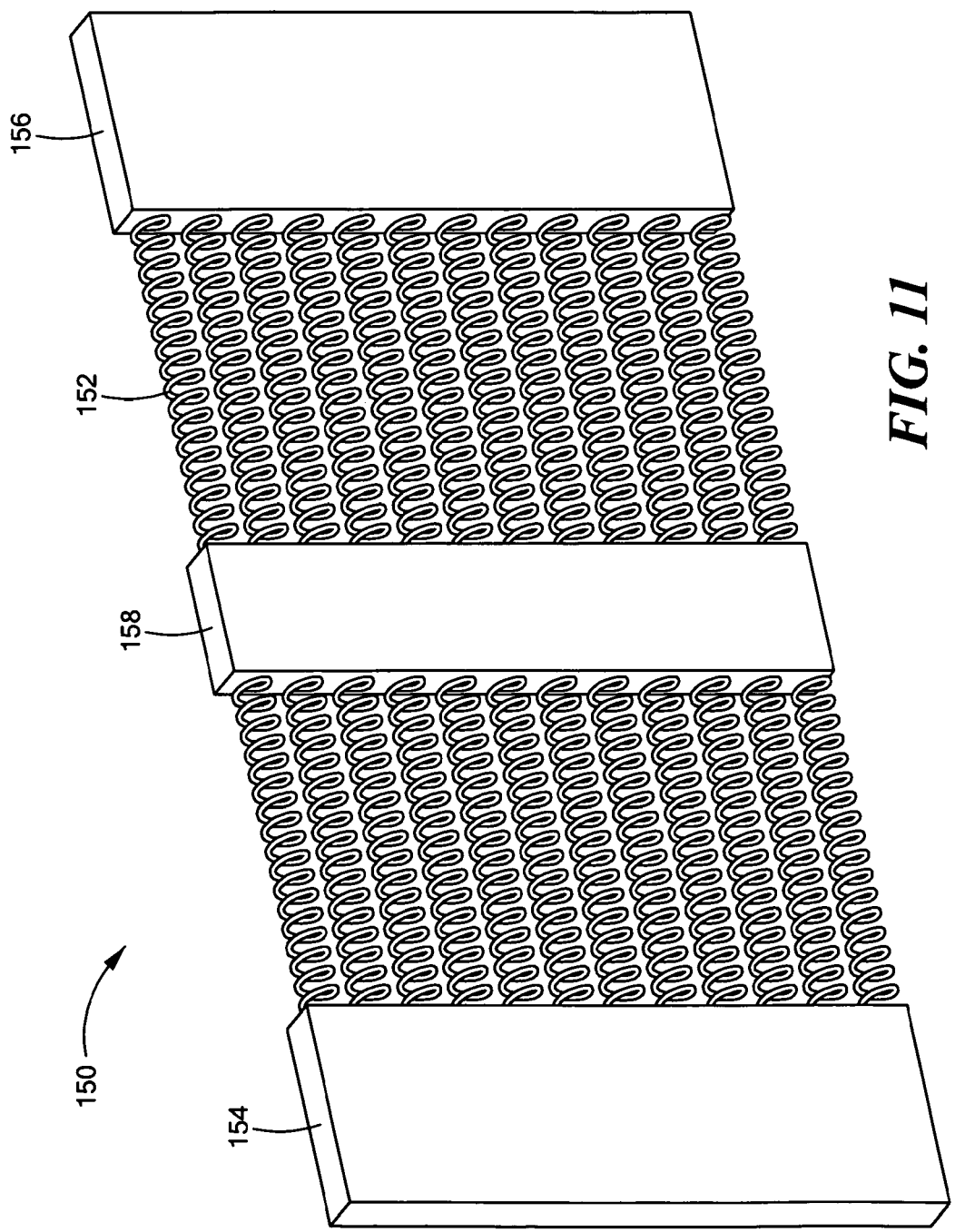
FIG. 11 is a diagram of an illustrative SMA actuator cartridge in accordance with described embodiments.

FIG. 11 shows an illustrative SMA actuator cartridge 150. As shown, SMA actuator cartridge 150 might include: a singular, extended, and de-twinned SMA coil 152 that is held within two polymer end caps 154 and 156 and central polymer spacer 158. In at least one implementation, end caps 154 and 156 and central spacer 158 are formed by a 3-dimensional (3D) printer, although other construction techniques might alternatively be used. As shown in FIG. 11, SMA coil 152 is laced between the end caps 154 and 156 through central spacer 158 twelve times, resulting in actuator cartridge 150 having twelve (12) parallel coils that are equally spaced. As will be appreciated, any number of parallel coil segments might be used in any particular implementation. Because SMA actuator cartridge 150 is comprised of a singular actuator 152 (instead of 12 individual actuators), both electrical conductivity and actuator structural integrity are guaranteed (i.e., the series circuit cannot be compromised unless the actuator wire breaks, and no actuators can individually pull free of the structure, barring failure of the wire or end cap structure itself). In addition, given the flexibility in design of the 3D-printed end caps, a variety of designs are possible for mating the cartridge to adjoining passive fabrics.

Although described as employing a singular SMA coil 152, it should be appreciated that SMA actuator cartridges that include multiple separate SMA coils may also be provided in different embodiments. In such implementations, the multiple separate SMA coils can be held in a substantially parallel arrangement within the SMA actuator cartridge. Also, in some implementations, multiple intermediate spacer elements might be provided between end caps 154 and 156 in a cartridge structure, rather than a single central spacer 158 as shown in FIG. 11. Alternatively, two end caps can be used within a cartridge without an intermediate spacer element.

Figure 12:
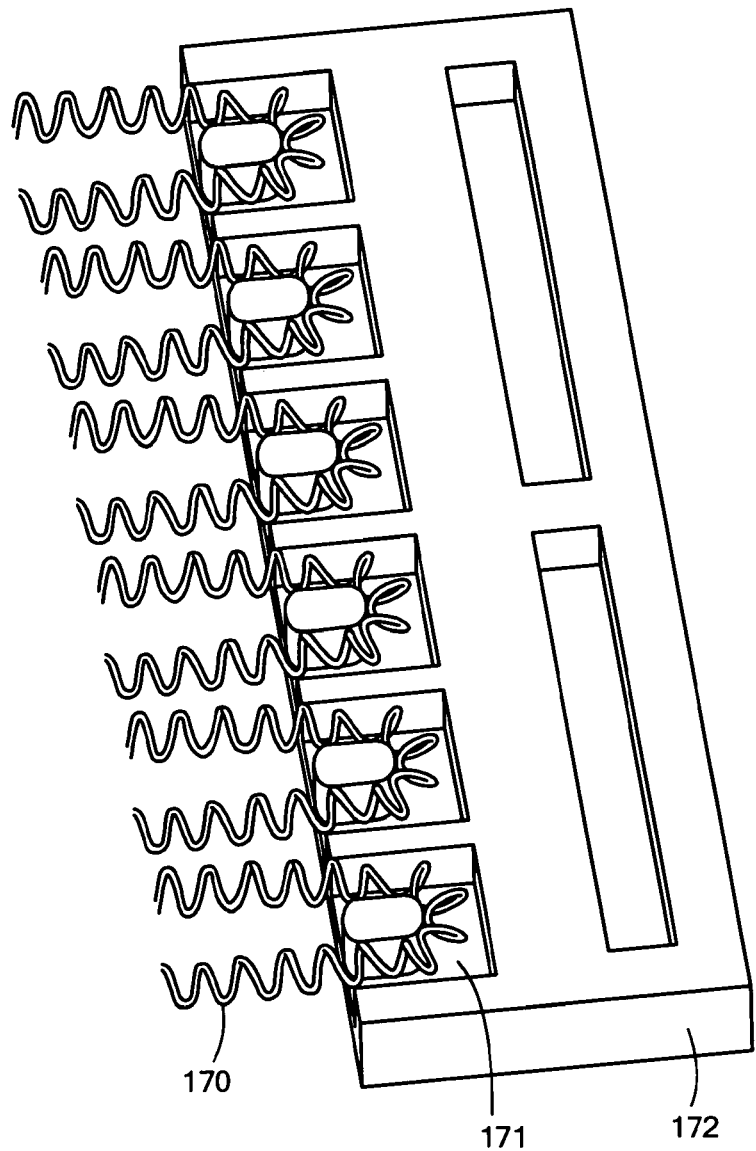
FIG. 12 is a diagram of an SMA coil embedded within the channels of a partially formed end cap of an SMA actuator cartridge in accordance with described embodiments.

In a first technique for manufacturing SMA actuator cartridge 150, a single-plastic, fully embedded SMA cartridge is provided using 3D printing. SMA actuator cartridge 150 is fully encased in homogeneous Acrylonitrile Butadiene Styrene (ABS) plastic in a single step, part way through the 3D printing build phase. The 3D printed end caps and spacer have narrow channels (i.e., channels having a smaller diameter than that of the SMA coil) in which the SMA coil is forcibly laced/embedded during manufacturing of the cartridge. This may be performed using, for example, a manual tool to force the coil into each channel to lock it in place, or by an automated process. For example, FIG. 12 shows illustrative SMA coil 170 embedded within channels 171 of partially formed end cap 172. Once SMA coil 170 is embedded within channels 171 of end cap 172, the 3D print is resumed, and several layers of ABS plastic are deposited over the top the actuator cartridge to encase (fully or partially) the coil in place.

FIGS. 13 and 14 show illustrative end caps 180 and illustrative central spacer 182 at a pre-completion stage (FIG. 13) and a completion stage (FIG. 14). In the embodiment shown in FIGS. 13 and 14, a single type of plastic material (e.g., ABS) might be employed. To simplify illustration, SMA coil (e.g., coil 170) is not shown. As shown in FIGS. 13 and 14, end caps 180 include openings 184 to mate the cartridge to adjoining passive fabrics, although other mating structures might alternatively be used.

Figure 15:
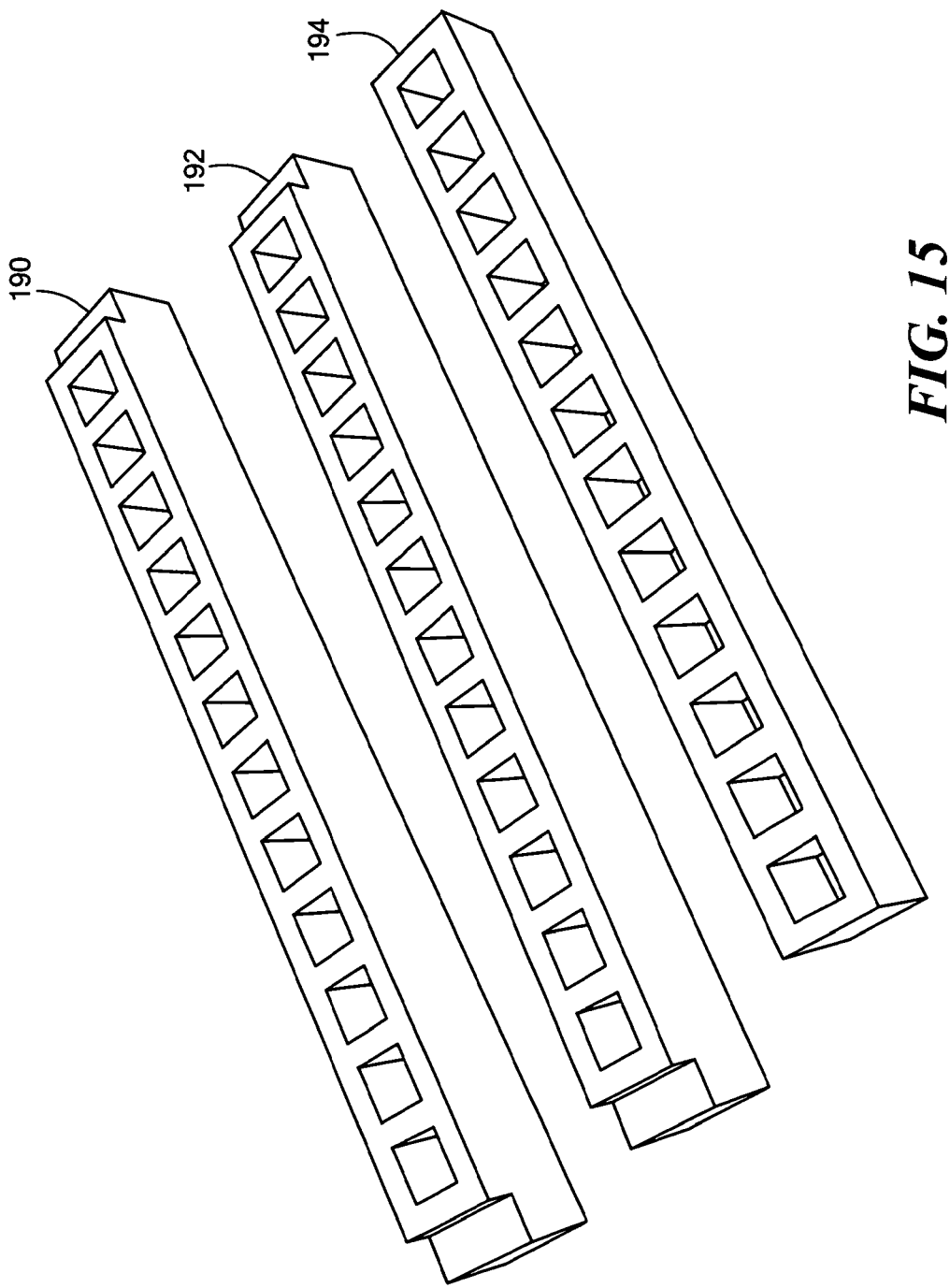
FIGS. 15 and 16 are diagrams of illustrative end caps and an illustrative central spacer for an SMA actuator cartridge in accordance with described embodiments.
Figure 16:
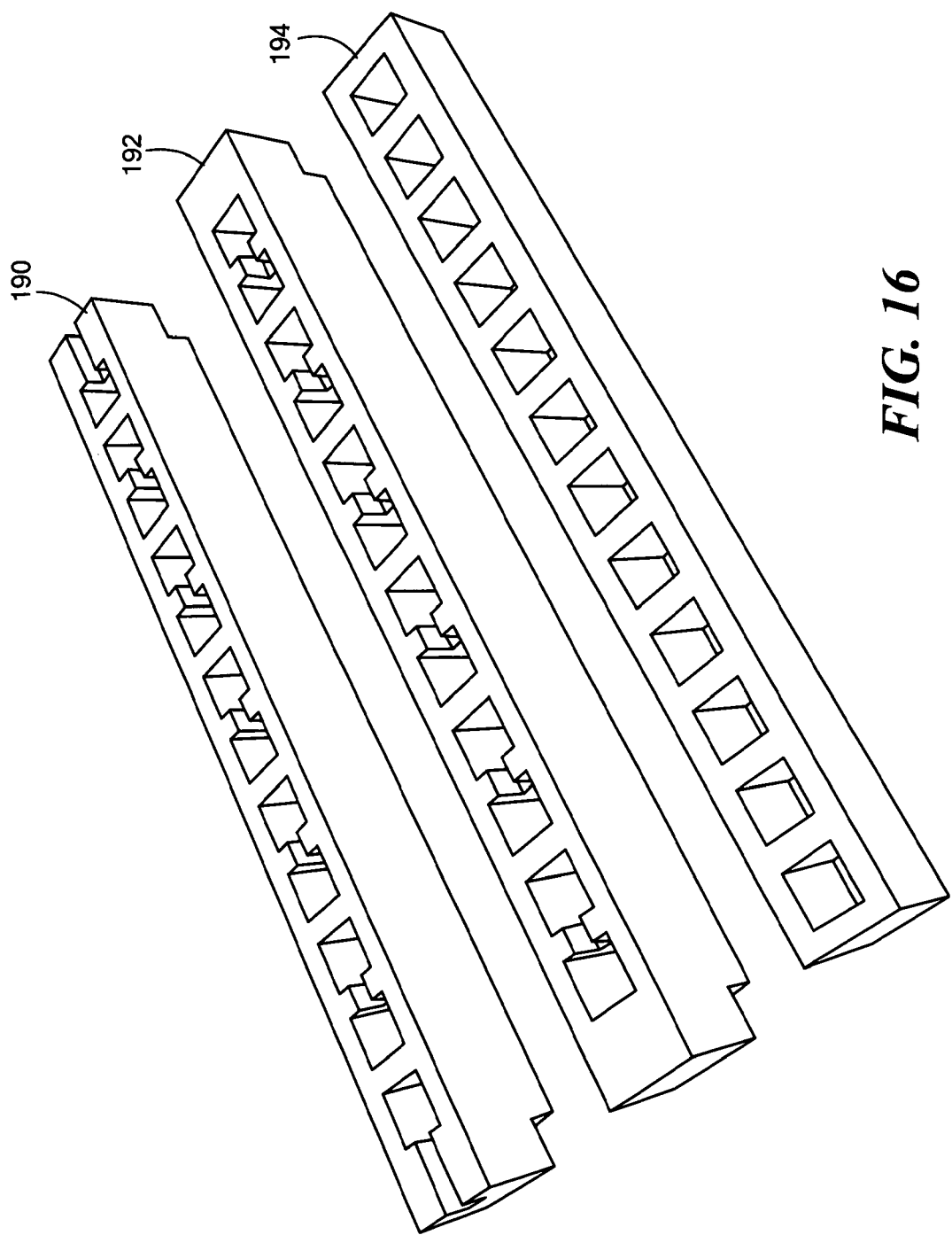

In a second technique for manufacturing SMA actuator cartridge 150, a multi-plastic, two-piece SMA cartridge is provided. Using this approach, three 3D printed structures (two end cap channel insets and a central spacer) are designed with wide channels that are wider than the diameter of the SMA coil. The SMA coil is loosely laced through these structures resulting in an unfinished cartridge that resembles the final cartridge dimensions, but with little structural stability. The channels are wider than the coil diameter to ensure that it is possible to lace the coil through the finished channels (post-fabrication). The end caps and central spacer may be prefabricated using a high temperature plastic (e.g., a Fused Deposition Modeling (FDM) thermoplastic, such as, for example, ULTEM 9085 or the like). FIGS. 15 and 16 are a top view and a bottom view illustrating exemplary designs of end caps 190 and 192 and central spacer 194 for a multi-plastic cartridge in accordance with an embodiment.

Figure 17:
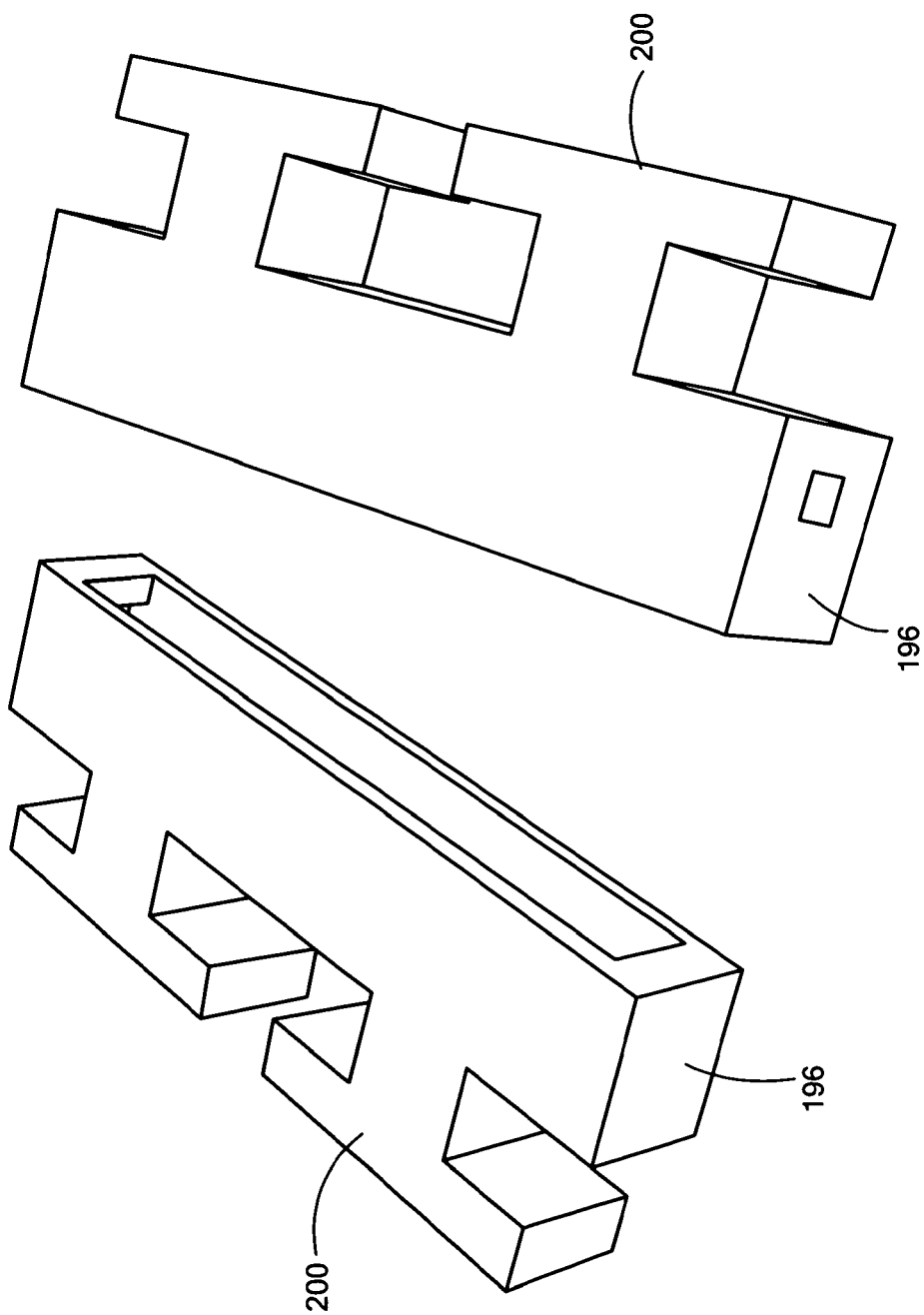
FIGS. 17 and 18 are diagrams of illustrative end cap superstructures in accordance with described embodiments.
Figure 18:
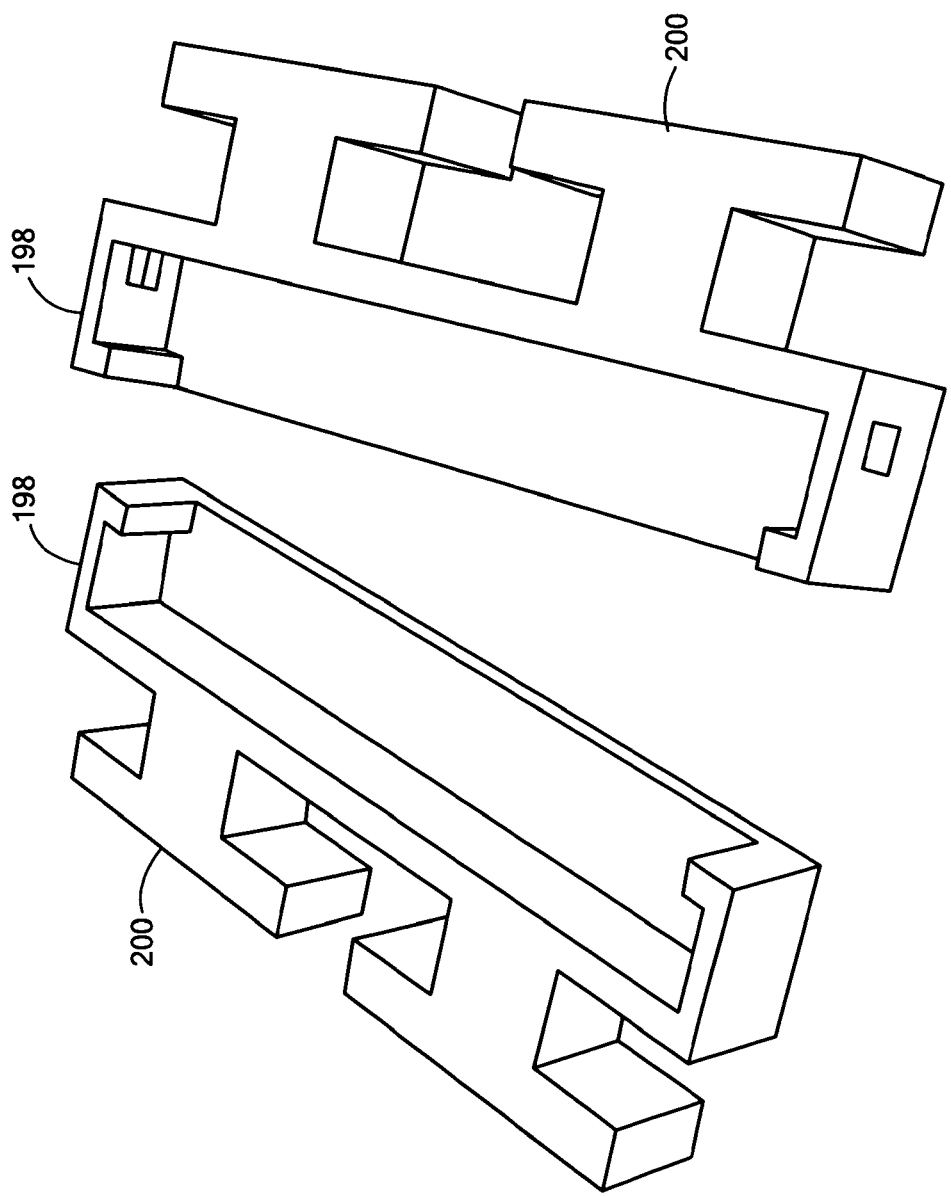

In addition to the end caps and central spacer, 3D printed ABS end cap superstructures are provided with a strategically designed cavity that matches the shape of the end cap insets. As is done in the single-plastic method described above, the 3D print build can be paused part way through the process and the end cap insets with the interlaced SMA coil are inserted into respective cavities of the ABS end cap superstructures. Once this is completed, the build is resumed, thus encasing and fixing the ULTEM end cap insets in the ABS end cap superstructures. FIGS. 17 and 18 illustrate exemplary designs of end cap superstructures 196 and 198 in accordance with different embodiments. As shown, the end cap superstructures 196 and 198 include protrusions 200 to facilitate connection of the resulting cartridge to a passive fabric material.

While both of the above-described fabrication techniques produce functional actuators, they differ in terms of their relative structural stability, actuator spacing, and durability. The single-plastic method, for example, produces a structurally superior and simpler actuator, due to several factors: first, the end caps are made in a single build and of a single material. Second, the actuators are physically locked in place both by friction and as a result of being encased in plastic during the build. Third, the structure is more resilient to cracking and other failures than the multi-plastic design. In addition, because the actuator can be embedded when the structure is incomplete (allowing for much narrower channels than would otherwise be feasible), the actuator spacing approaches the physical limit given the capabilities of current 3D printers. For example, in a 1-inch wide cartridge, assuming a minimum wall width of 0.03" between actuator segments, it is possible to fit 12.65 actuator segments of the above-described size in the cartridge. Conversely, the multi-plastic cartridge can only pack 12 actuators into a 1.485" width, which is a significantly smaller packing density.

However, the single-plastic design can fail in some instances during SMA activation as a result of the ABS plastic exceeding its glass transition temperature ($T_g$=105° C.). This glass transition temperature is significantly lower than the SMA austenite finish temperature. The multi-plastic design, on the other hand, is not susceptible to thermally induced failure as the ULTEM glass transition temperature ($T_g$=186° C.) is greater than the SMA austenite finish temperature. In effect, the ULTEM end cap insets shield the ABS superstructure from high temperatures during activation, preventing thermally induced structural failure. However, the thermal stability comes at the expense of certain structural stability. That is, the ABS end cap superstructures in the multi-plastic cartridges were found to crack more easily than their single-plastic counterparts, due to stress concentrations at the ULTEM-ABS.

In various embodiments, SMA actuator cartridges such as those described above, are coupled to passive textile materials to produce compression garments and the like. For example, in some embodiments, SMA actuator cartridge 150 of FIG. 11 might be coupled to opposite ends of a fabric member to form a tourniquet (e.g., similar to tourniquet 70 of FIG. 5). SMA actuator cartridge 150 might be used to develop other types of compression garments, for example, to replace the SMA actuators in many of the compression garment arrangements previously discussed.

In some embodiments, SMA actuator cartridges are incorporated with passive textiles to form mechanical counterpressure (MCP) space suits or other full body compression suits. In these applications, the mobility of the suits can be improved by strategically designing the suits to exploit the skin's natural lines of non-extension (LoNE). These lines represent contours on the human body that do not change length during natural motion (meaning as the skin stretches and deforms during movement, no tension or compression forces act along these specific contours). In some implementations, the integrated elements may be aligned with LoNE contours to provide wiring and pressure production capabilities that do not interfere with the mobility of the wearer. Other types of compression garments that utilize SMA actuator cartridges and other SMA actuator structures also exist.

For example, to make a practical compression suit, the restraint patterns of the garment might beneficially be aligned with the natural lines of non-extension (LoNE) of the wearer's body. These lines, which map contours of minimum stretch/contraction of the human skin as the body moves through its range of motion, signify potential patterns for any semi-rigid structural elements of the garment. By integrating such elements along the LoNE, the elements are less likely to be exposed to significant in-line stresses during movement of the wearer.

Illustrative techniques for identifying LoNEs of a wearer for designing a garment are described in related U.S. patent application Ser. No. 13/274,992 filed Oct. 17, 2011, and Ser. No. 14/837,455 filed Aug. 27, 2015, and International Patent Application No. PCT/US2015/053978 filed Oct. 5, 2015, which are commonly owned with the present application, and the teachings of which are hereby incorporated by reference herein. For example, fabrics for various areas of a garment might be selected based on fabric properties and the range of strain experienced at locations of the wearer's body during motion. For example, areas experiencing low magnitudes of strain could employ more rigid materials, while areas experiencing higher magnitudes of strain might employ more flexible materials. Areas with larger deformations should have materials that are less stiff to avoid adversely affecting mobility. The directionality of the strain field could be used to align and orient fabrics, seams or material properties, for example to locate garment seams in the locations of determined LoNEs, including the active seam structures described herein. Matching the deformation of the suit with the deformation of the skin of the wearer can reduce friction and increase comfort to provide a garment that provides compression and is wearable for extended periods of time.

In some embodiments, an SMA actuator cartridge is provided that includes a locking mechanism to hold the cartridge in a compressed state after compression has occurred. In some implementations, the locking mechanism of the cartridge will remain in the locked state after compression even if the stimulus is subsequently removed. In this manner, the cartridge is able to maintain the forces, tensions, and pressures produced by the contracted actuator (s) without requiring ongoing signal application. As will be appreciated, this arrangement can result in significant energy and cost savings in some applications by reducing the energy needed to provide stimuli to the cartridge, as well as in increasing safety for the wearer by introducing a fail-safe mechanism.

Figure 19:
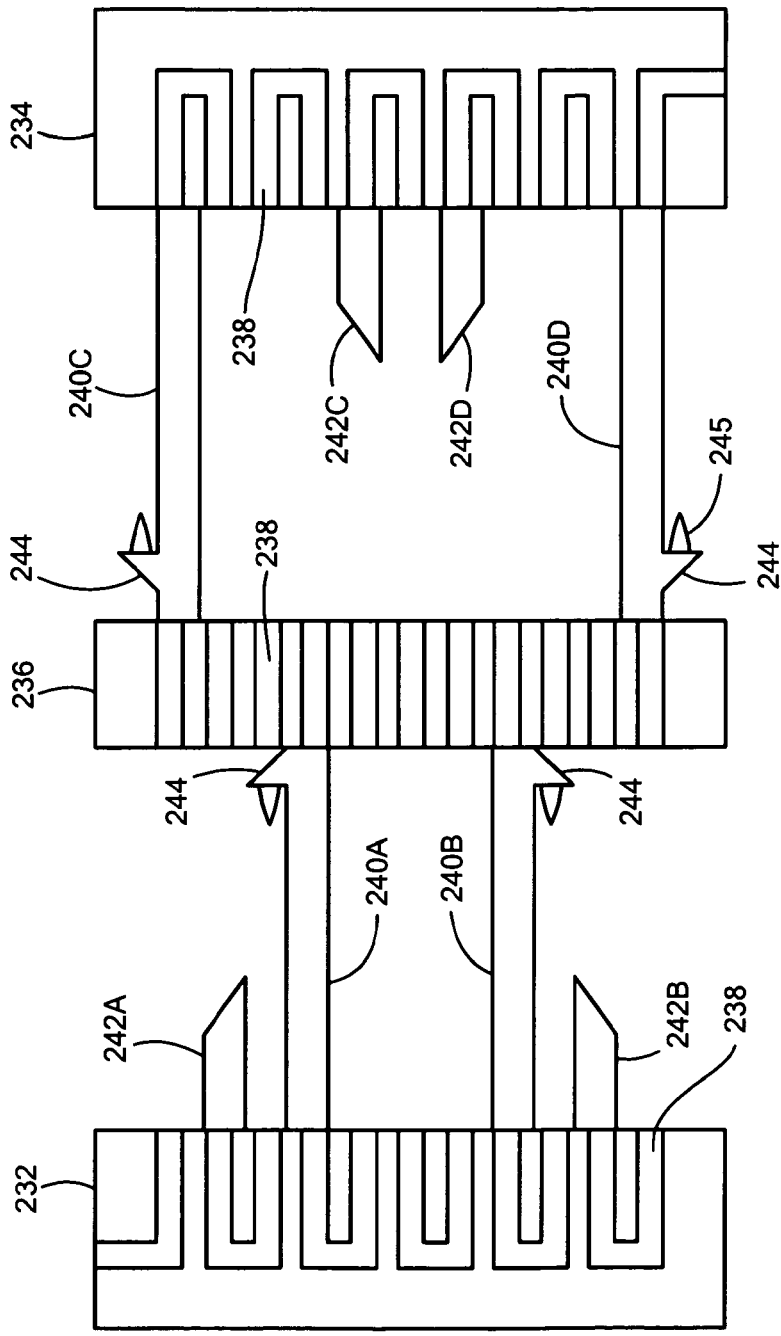
FIGS. 19 to 22 are diagrams of an illustrative SMA actuator cartridge having a locking mechanism in accordance with described embodiments.
Figure 20:
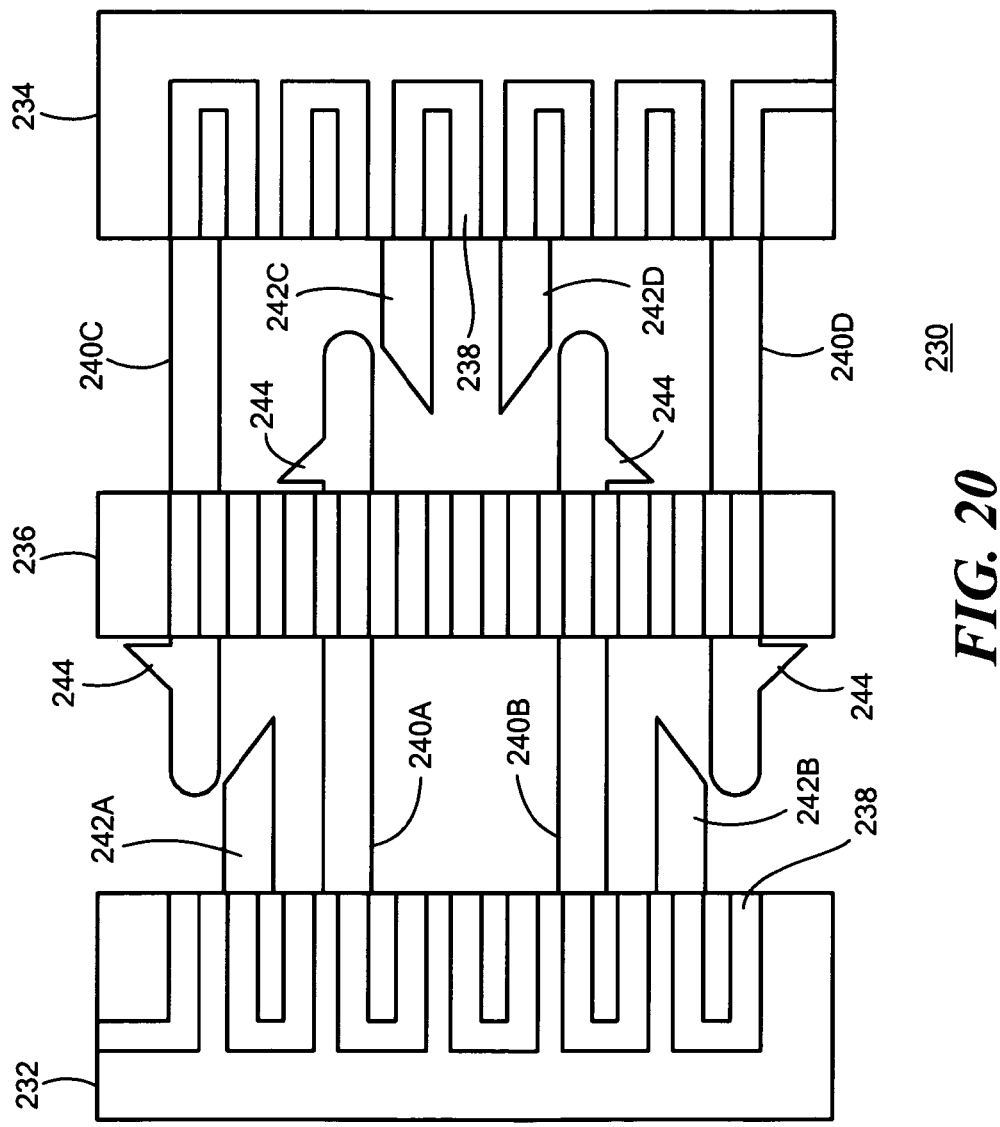

FIGS. 19, 20, 21 and 22 show an illustrative SMA actuator cartridge 230 having a locking mechanism. FIG. 19 shows a top view of cartridge 230 in an expanded state. FIG. 20 shows a top view of cartridge 230 in a contracted and locked state. In each of FIGS. 19 and 20, cartridge 230 is shown without SMA actuator coils to permit better illustration and understanding of the locking structures. As shown in FIG. 19, cartridge 230 includes first end cap 232, second end cap 234, and central spacer 236. As in SMA actuator cartridges described previously, first and second end caps 232 and 234 and central spacer 236 each include various channels 238 into which one or more SMA actuator coils are placed. Various coil segments may run back and forth between end caps 232 and 234 and through central spacer 236. As described, a single actuator coil or multiple actuator coils might be used. First and second end caps 232 and 234 and central spacer 236 might be fabricated using any of a variety of techniques including, for example, the single-plastic and the multi-plastic techniques described above.

Figure 21:
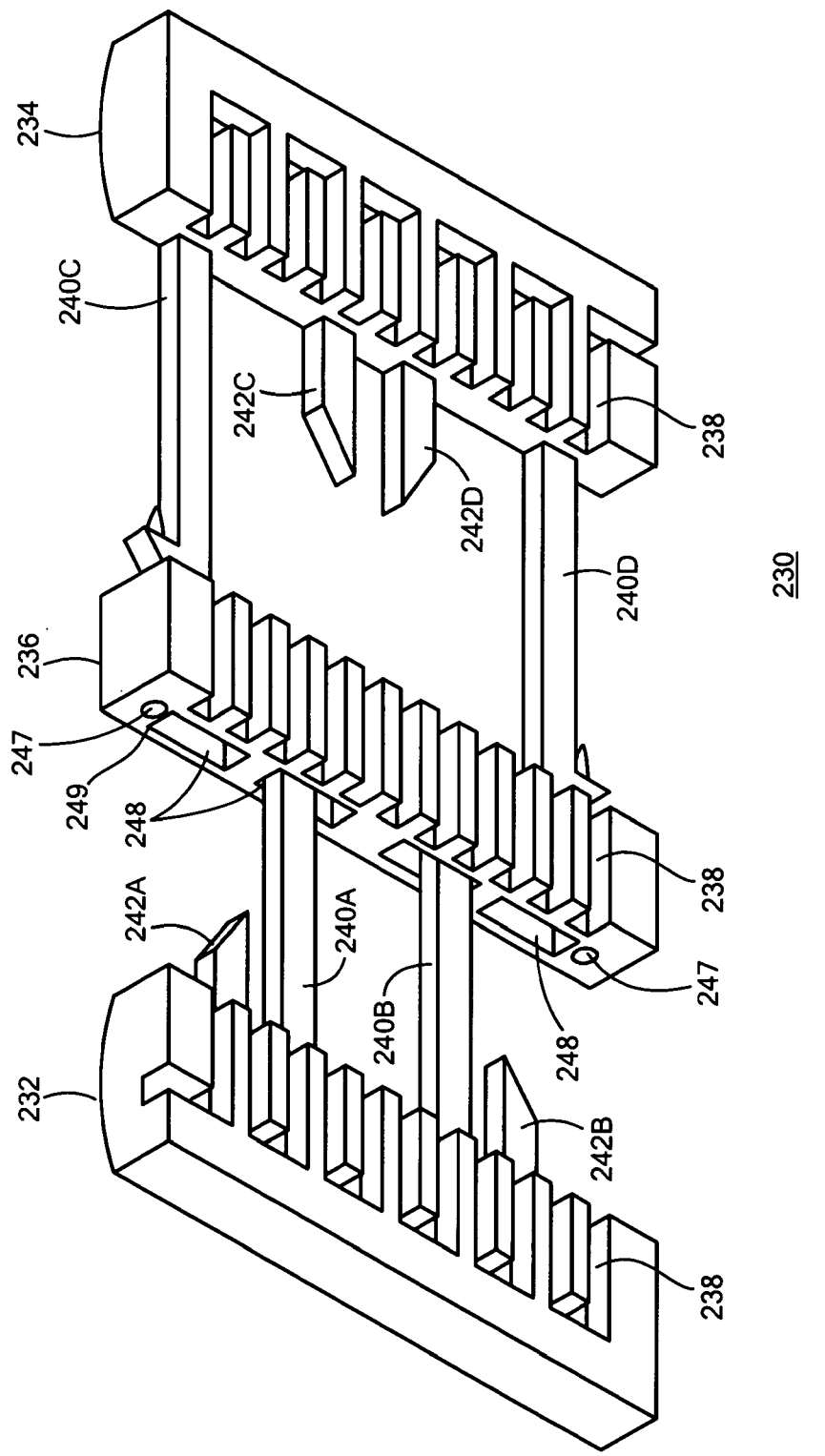

As shown in FIG. 19, first and second end caps 232 and 234 each include one or more locking arms, shown as locking arms 240A, 240B, 240C and 240D. As shown, locking arms 240A, 240B, 240C and 240D each include locking tab 244 disposed near a distal end of the locking arm. Locking arms 240A, 240B, 240C and 240D of the end caps 232 and 234 fit through slots within central spacer 236 during normal cartridge operation. FIG. 21 is an isometric view of cartridge 230 showing slots 248 of central spacer 236 with locking arms 240A, 240B, 240C and 240D inserted therein. In addition to the locking arms, end caps 232 and 234 each also include one or more shorter arms, shown as arms 242A, 242B, 242C and 242D. As shown, each of the shorter arms 242A, 242B, 242C and 242D might have an angled end.

Referring back to FIG. 19, cartridge 230 is shown in an expanded (unlocked) state. Ends of locking arms 240A, 240B, 240C and 240D are within slots 248 of central spacer 236, but end caps 232 and 234 are separated (e.g., the active seam structure is open) with the SMA actuator coil(s) (not shown) in an expanded state. FIG. 20 shows cartridge 230 in a compressed (and locked) state. The compressed and locked state might be reached by applying stimulus to the SMA actuator coil(s) and allowing the coil(s) to contract to a memory state. This action pulls end caps 232 and 234 together and eventually locks end caps 232 and 234 to central spacer 236 by pushing locking tabs 244 through slots 248 to engage central spacer 236. Once locked, cartridge 230 will remain locked even if the stimulus is subsequently removed due to the physical engagement of locking tabs 244. In some implementations, manual action might be required to unlock cartridge 230 once locked.

When the stimulus is applied to the SMA actuator and end caps 232 and 234 are pulled together, sloped edges of locking tabs 244 engage corresponding edges 249 of slots 248 (see FIG. 21), and the sloped edges slide through slots 248 while also pushing upon the sloped edges of locking tabs 244. This pushes the locking arms 240A, 240B, 240C and 240D inward toward each other as end caps 232 and 234 are drawn together. Eventually, locking tabs 244 fully emerge from the other side of slots 248 of central spacer 236 and snap into a locked position. In the locked position, the flat sides of locking tabs 244 engage the wall of central spacer 236 and thus prevent locking tabs 244 from re-entering slots 248. Cartridge 230 is thus locked in the compressed position. In some embodiments, cartridge 230 remains in the locked position until end caps 232 and 234 are pulled outwardly (i.e., in a direction to open the seam) with sufficient force to overcome the interaction between locking tabs 244 and the wall of central spacer 236.

Figure 22:
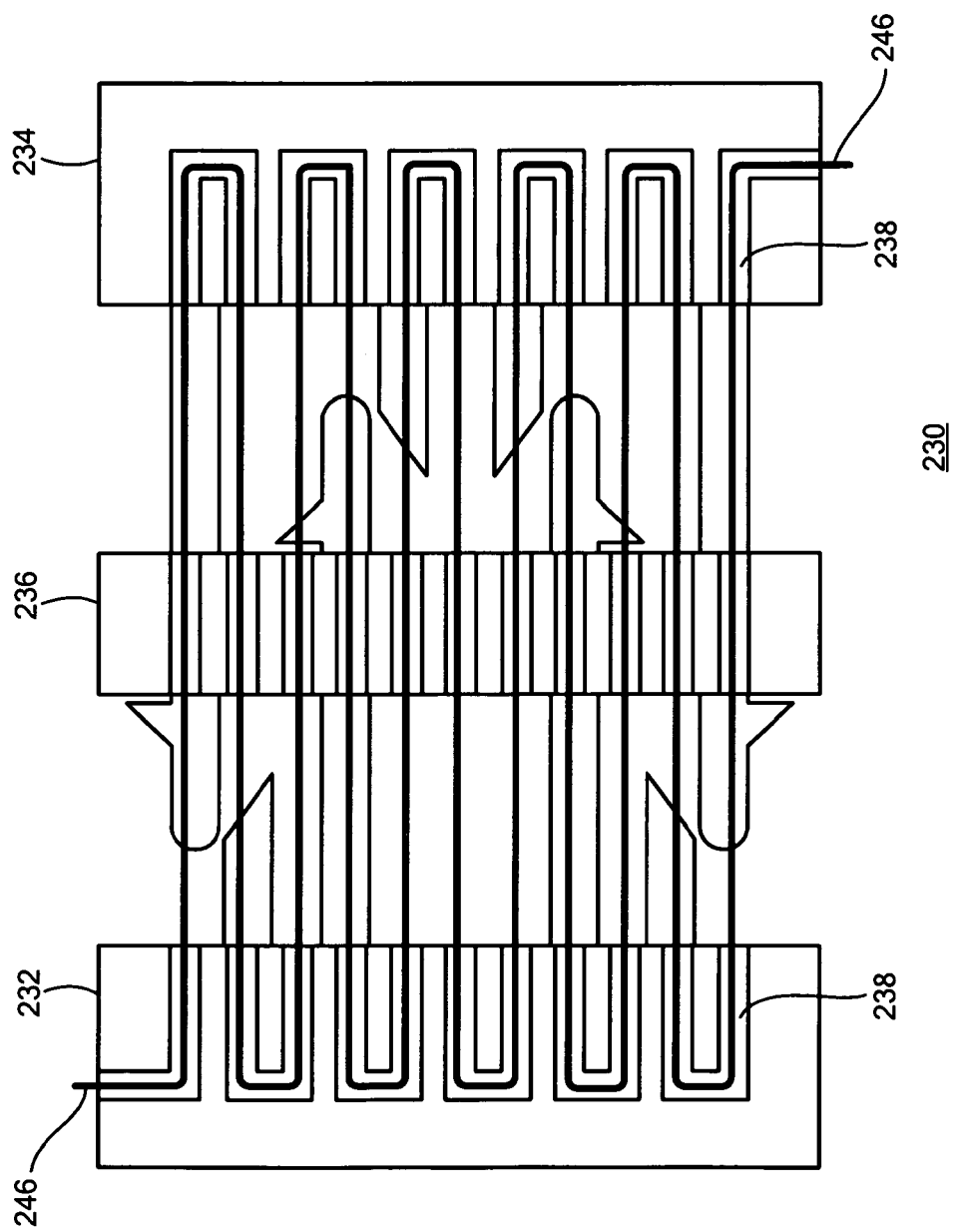

As shown in FIG. 20, in the locked position, the shorter arms 242A, 242B, 242C and 242D on end caps 232 and 234 line up with ends of corresponding locking arms 240A, 240B, 240C and 240D to prevent the locking arms from disengaging. In some embodiments, the shorter arms 242A, 242B, 242C and 242D might not be included. FIG. 22 is a top view of cartridge 230 with SMA actuator coil 246 inserted within the channels 238. FIG. 22 shows cartridge 230 in a contracted (and locked) state. Although illustrated with the channels 238 visible from the top in FIGS. 19, 20, 21 and 22, it should be appreciated that cartridge 230 will typically have a cover member covering channels 238 as shown in FIG. 14.

Although illustrated in FIGS. 19, 20, 21 and 22 with the locking arms associated with the end caps 232 and 234 and fitting into slots 248 in central spacer 236, it should be appreciated that other locking arrangements may alternatively be used. For example, in one alternative approach, locking arms might be implemented on central spacer 236 and corresponding slots might be formed within end caps 232 and 234 to receive the locking arms. In another alternative, locking arms might be implemented on both end caps 232 and 234 and central spacer 236. In some embodiments, central spacer 236 might not be used and locking arms on one of end caps 232 and 234 might lock in slots of the other one of end caps 232 and 234. Other locking mechanisms may alternatively be used within an SMA actuator cartridge.

Figure 23:
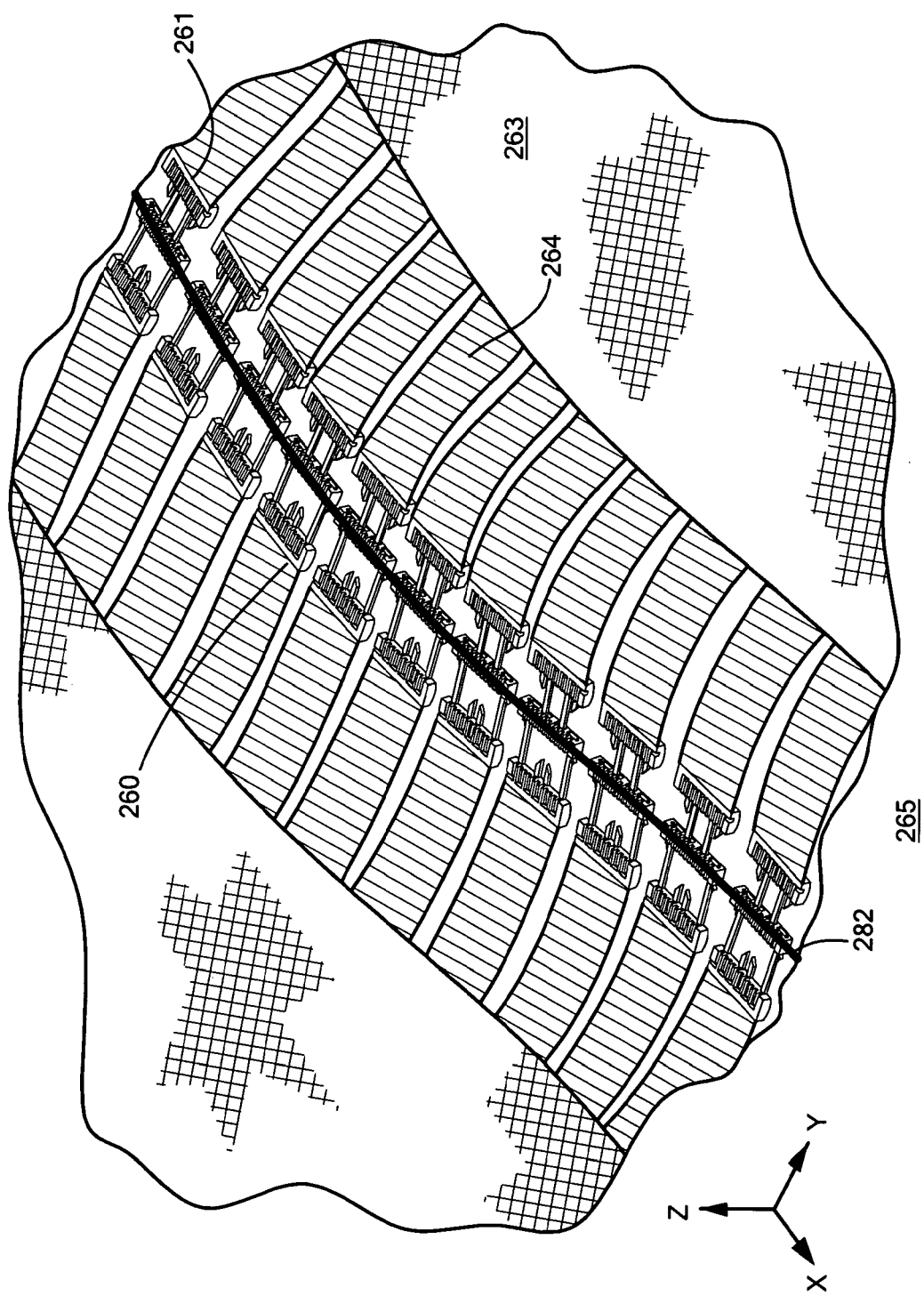
FIGS. 23 and 24 are diagrams of an illustrative seam structure formed by a plurality of locking cartridges in accordance with described embodiment.
Figure 25:
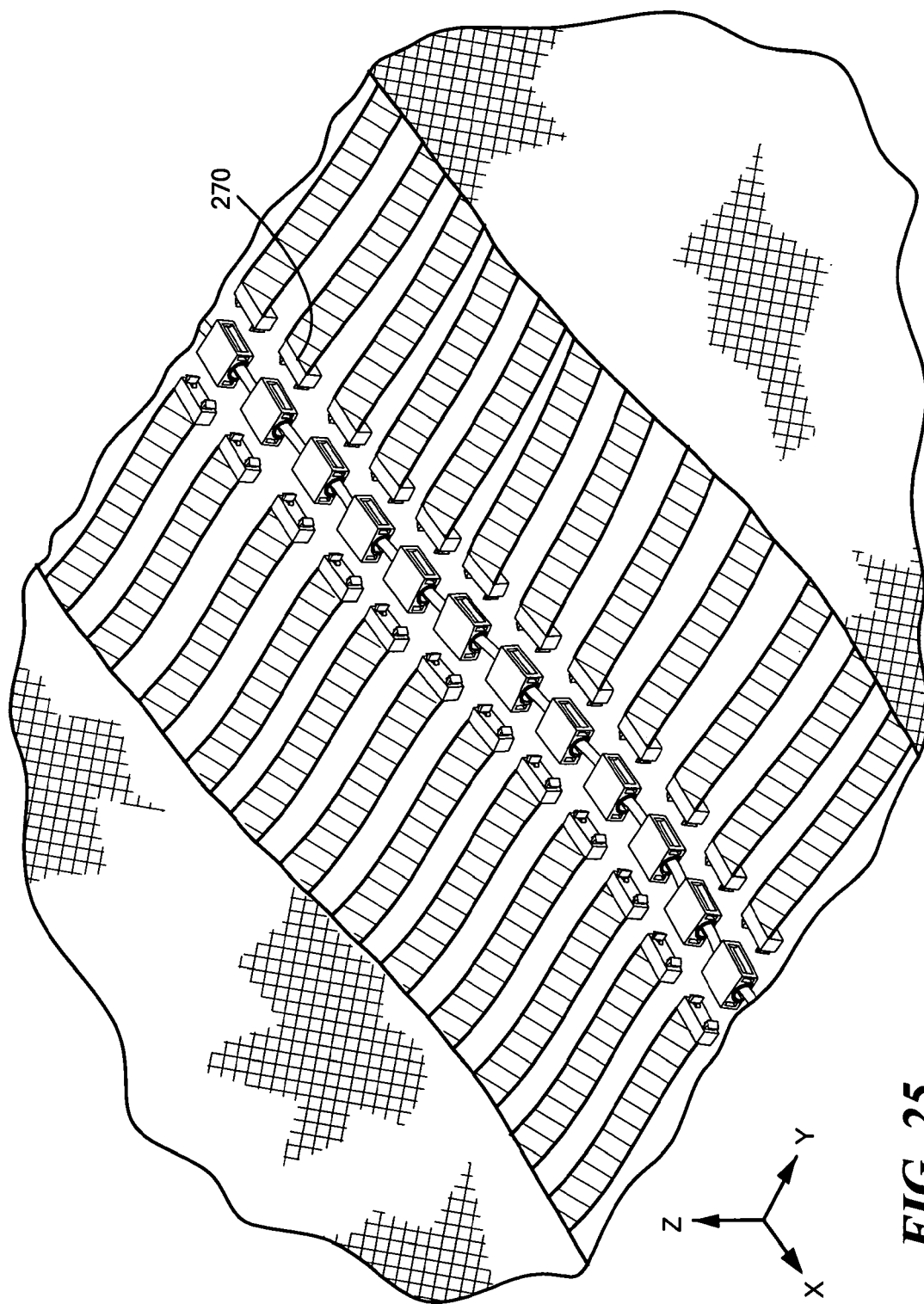

In some embodiments, a plurality of SMA cartridges can be coupled in parallel to form a seam (e.g., 265) of a compression garment or other structure. FIGS. 23 and 25 show illustrative arrangements utilizing a plurality of cartridges 260 having locking mechanisms. As shown, the cartridges might be coupled along a steel cable or other backbone structure (shown as 282). Cartridges 260 might typically be coupled such that a stimulus is provided to all cartridges at the same time to close the seam and provide compression. In some implementations, the cable (e.g., 282) provides an electrical stimulus to the SMA actuators within the various cartridges 260. Other techniques and/or structures might alternatively be used for providing the stimulus.

As shown in FIG. 23, seam structure 265 is coupled to textile materials 263 to form a compression garment for a body part (e.g., an arm, etc.) of a wearer. As shown, fabric strips 264 may be connected between garment material 263 and ends of cartridges 260 of seam structure 265. The lengths of fabric strips 264 might be selected to be fitted to a particular wearer or a particular compression. One or more coupling structures are provided to penult the ends of fabric strips 264 to be secured to end caps 261 of corresponding cartridges in seam structure 265. In some embodiments, cabling 282 within seam structure 265 of a compression garment follows a Line of Non-Extension (LoNE) of the corresponding wearer. For simplicity of illustration, the locking cartridges 260 of FIG. 23 are shown without SMA actuator coils. In addition, cartridges 260 are shown without tops. It should be appreciated that these structures will typically be deployed with cover members covering the SMA actuator channels. One or more additional fabric covers may also be provided over the seam structure to provide protection to the underlying cartridges.

Figure 24:
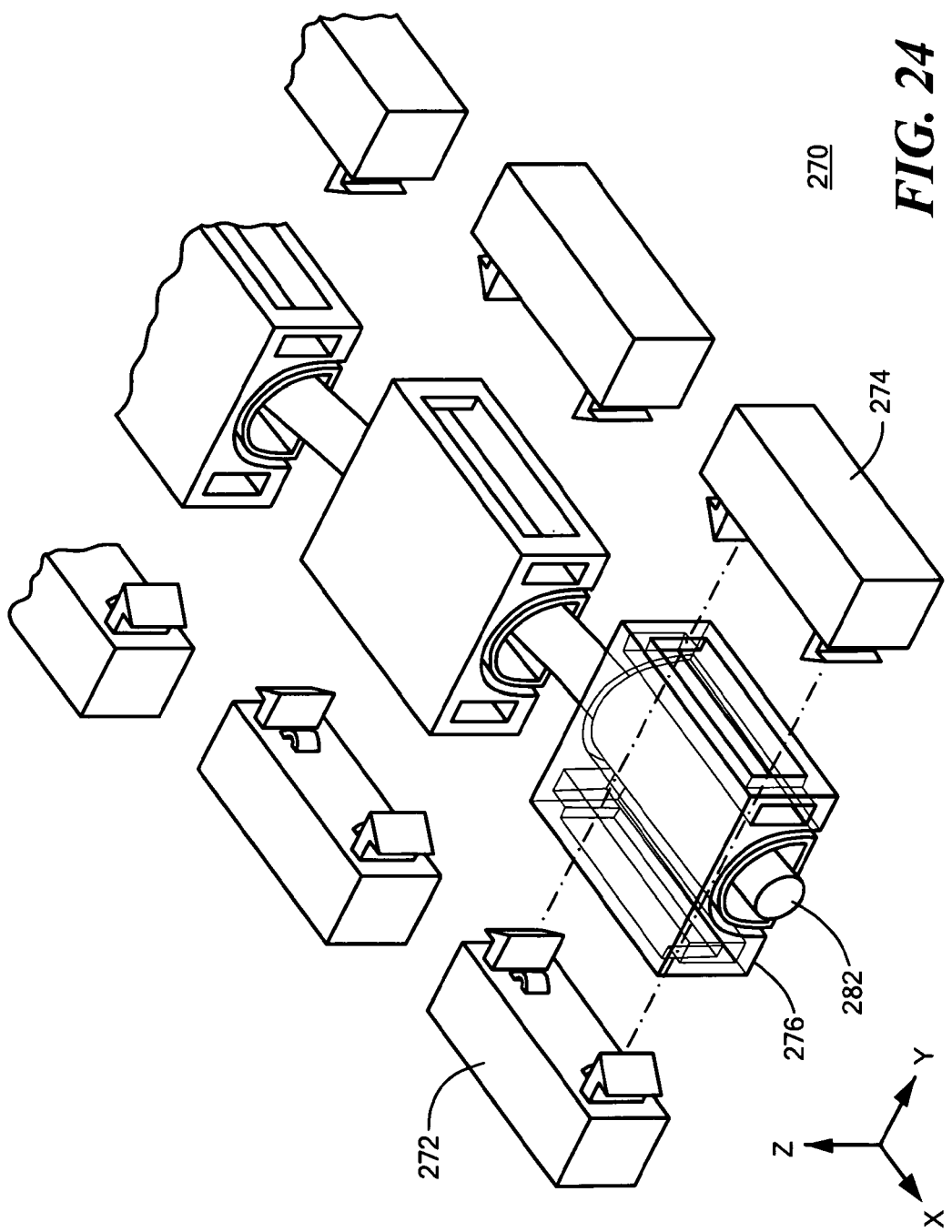

FIG. 24 shows another illustrative locking cartridge 270. As shown, locking cartridge 270 might also be connected together to form a seam of a garment or other structure. As illustrated, cartridge 270 includes two end caps 272 and 274 and central spacer 276. Central spacer 276 includes opening 280 for insertion of cable 282 to form a backbone (or the like) for a corresponding compression garment, for example to form a seam along a LoNE of the wearer of the compression garment. In some embodiments, cable 282 might also facilitate the application of stimulus signals to the SMA coil(s) (not shown) of cartridge 270. As before, end caps 272 and 274 might include locking structures to lock cartridge 270 in a compressed state when a stimulus is provided and then removed. FIG. 25 shows a plurality of cartridges 270 coupled together to form a seam of a compression garment. As shown in FIG. 23, ends of a fabric strip are coupled to end caps 272 and 274 of each cartridge. The fabric strips might be sized so that the compression garment fits a particular wearer of interest and provides a desired compression.

Figure 26:
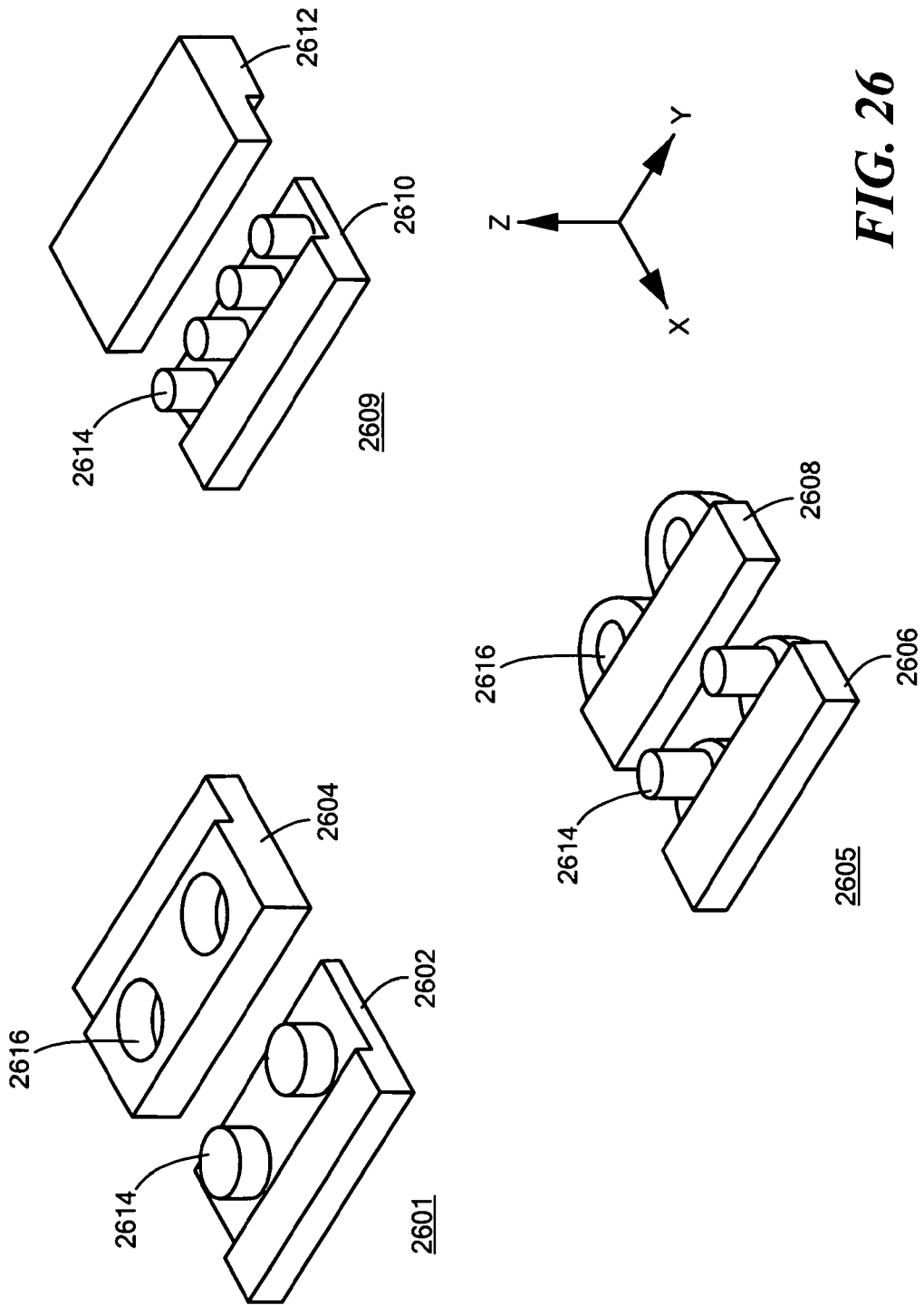
FIG. 26 is a diagram of illustrative mechanisms for attaching a passive fabric member to an SMA cartridge in accordance with described embodiments.

For use in compression garments and other structures, SMA actuator cartridges should provide a strong, reliable mechanism for attaching a passive fabric member to the cartridge. FIG. 26 shows various custom fabric attachment mechanisms that might be used with cartridges of the present disclosure. For example, FIG. 26 shows three illustrative mechanisms, 2601, 2605 and 2609, for attaching the SMA actuator cartridges to the passive fabric. As shown, each of mechanisms, 2601, 2605 and 2609 might include a first coupling member (e.g., 2602, 2606 and 2610, respectively) that includes one or more lugs (e.g., 2614) that are received by corresponding wells (e.g., 2616) within a second coupling member. The one or more lugs and one or more corresponding wells might be employed to physically retain the passive fabric within the wells when the first and second coupling members are assembled. Other attachment schemes might alternatively be used. For example, common garment attachment structures, such as snaps, buttons, hook and loop, zippers, stitching, buckles, and other garment attachment structures might be employed.

Figure 27A:
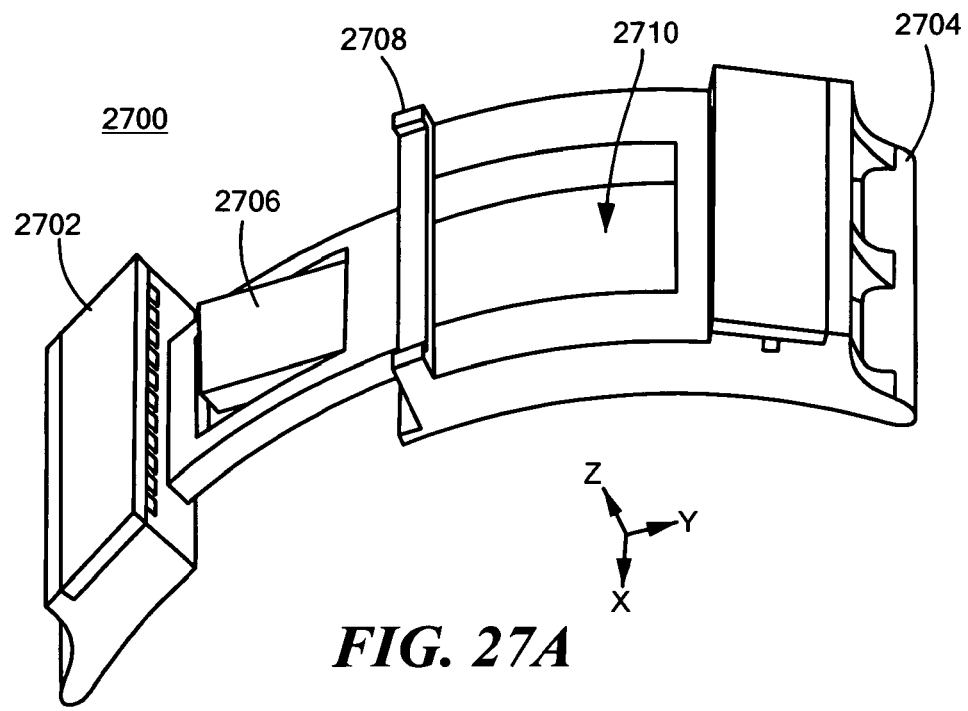
FIGS. 27A, 27B, 27C and 27D are diagrams of another illustrative SMA actuator cartridge having a locking mechanism in accordance with described embodiments.
Figure 27B:
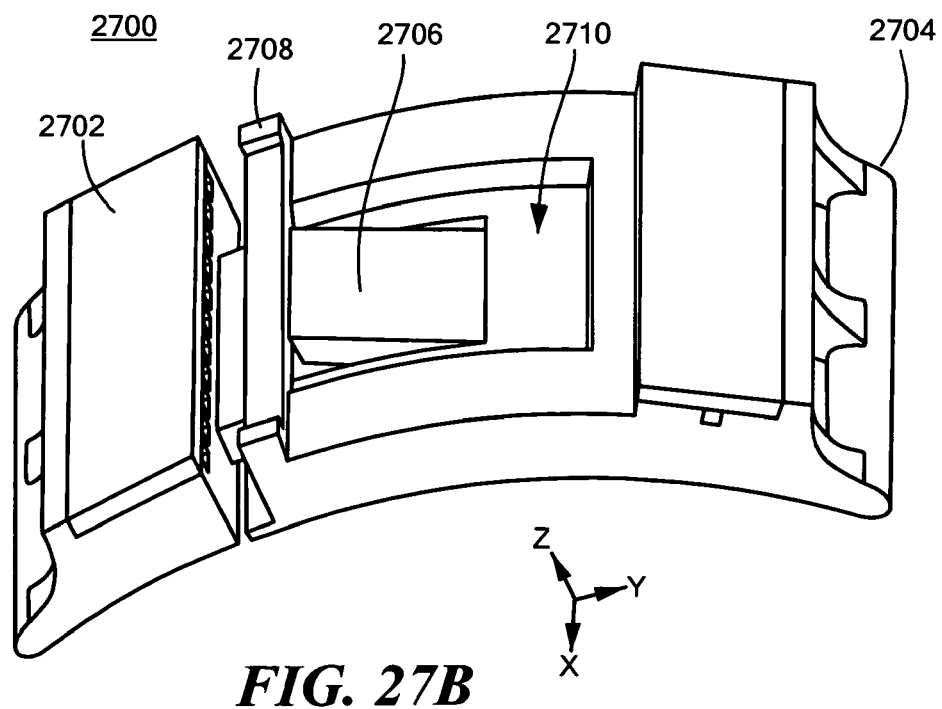
Figure 27C:
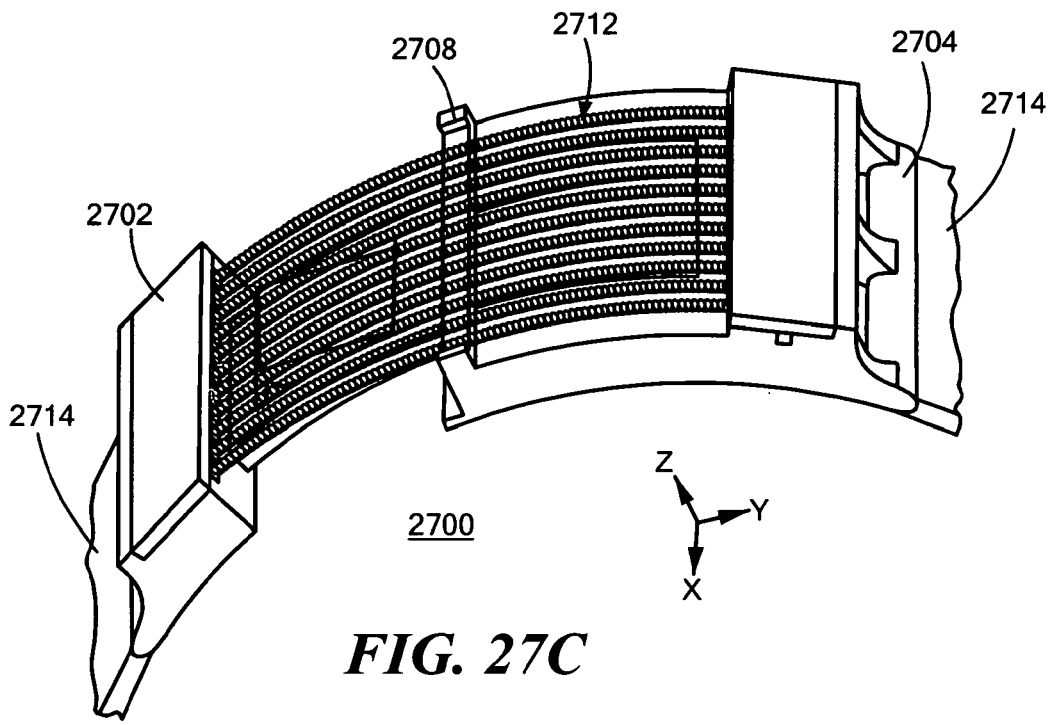
Figure 27D:
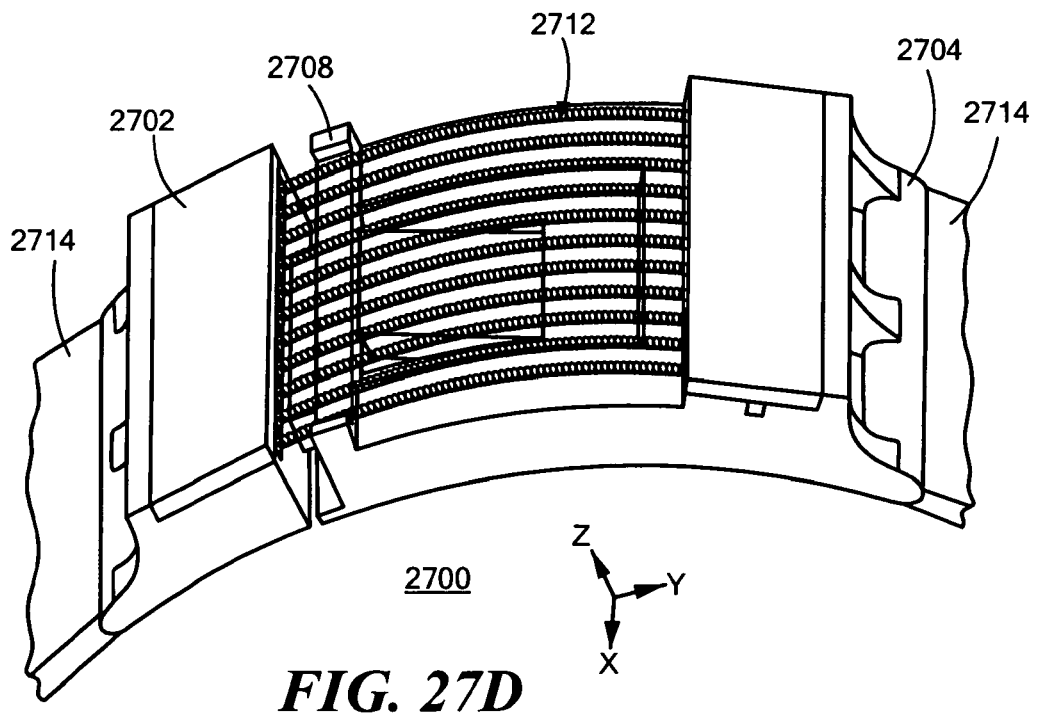

FIGS. 27A-27D show an illustrative SMA actuator cartridge 2700 having a locking mechanism. FIG. 27A shows a view of cartridge 2700 in an expanded state and FIG. 27B shows a view of cartridge 2700 in a contracted and locked state. FIGS. 27A and 27B show cartridge 2700 without any SMA coils, to permit better illustration and understanding of the locking structures. FIG. 27C shows a view of cartridge 2700 in an expanded state and FIG. 27D shows a view of cartridge 2700 in a contracted and locked state. FIGS. 27C and 27D show cartridge 2700 having SMA coils.

As shown in FIGS. 27A and 27B, SMA cartridge 2700 includes first end cap 2702 and second end cap 2704. As in SMA actuator cartridges described previously, first and second end caps 2702 and 2704 each include various channels (not shown in FIGS. 27A and 27B) into which one or more SMA actuator coils are placed. Various coil segments may run back and forth between end caps 2702 and 2704, as shown in FIGS. 27C and 27D. As described, a single actuator coil or multiple actuator coils might be used. First and second end caps 2702 and 2704 might be fabricated using any of a variety of techniques including, for example, the single-plastic and the multi-plastic techniques described above.

As shown in FIGS. 27A and 27B, first end cap 2702 includes locking tab 2706. Second end cap 2704 includes buckle 2708 that includes space 2710. When SMA cartridge 2700 is in a compressed and locked state, as shown in FIG. 27B, locking tab 2706 is pulled into space 2710 such that a rear side of locking tab 2706 engages a front side of side of buckle 2708, thereby locking end caps 2702 and 2704 together. Once locked, end caps 2702 and 2704 will remain locked even if the stimulus is subsequently removed due to the physical engagement of locking tab 2706 and buckle 2708. In some implementations, manual action might be required to unlock end caps 2702 and 2704, for example pressing upon locking tab 2706 so that it disengages from buckle 2708 and can be removed from space 2710.

When the stimulus is applied to the SMA actuator and end caps 2702 and 2704 are pulled together, a sloped edge of locking tabs 2706 slides into buckle 2708. This pushes the locking tab 2706 downward as end caps 2702 and 2704 are drawn together. Eventually, locking tab 2706 fully emerges into space 2710 and snaps into a locked position (e.g., as shown in FIG. 27B). In the locked position, the flat sides of locking tab 2706 engages buckle 2708 and thus prevents locking tabs 2706 from unlocking. Cartridge 2700 is thus locked in the compressed position. In some embodiments, cartridge 2700 remains in the locked position until end caps 2702 and 2704 are pulled outwardly (i.e., in a direction to open the seam) with sufficient force to overcome the interaction between locking tab 2706 and buckle 2708. In other embodiments, cartridge 2700 remains in the locked position until locking tab 2706 is pushed downwardly (e.g., along the Z axis defined in FIGS. 27A-D) with sufficient force to overcome the interaction between locking tab 2706 and buckle 2708.

FIGS. 27C and 27D show views of cartridge 2700 in a completed form having one or more SMA coils 2712. FIGS. 27C and 27D also illustrate material 2714 coupled to end caps 2702 and 2704, for example as part of a compression garment, tourniquet or the like as described herein.

Although described above as applying compression to body parts of wearers, it should be appreciated that the structures and techniques described herein may also be used to provide compression to structures in other compression applications. For example, the ability for a system to remotely constrict around an object has potential application in flow control (e.g., pumping systems), gasket/mechanical joining elements, as morphing surface coverings for robotic, aerospace, or architectural systems, and/or in other applications.

Although some structures discussed herein are described as applying compression to a single body part, or only a portion of a body part, it should be appreciated that the disclosed structures may be replicated and interconnected to generate full garments for users (e.g., a compressive shirt, compressive pants, a full body suit, etc.). Also, a single compression garment may be manufactured using multiple of the above-described active compressive structures in some embodiments.

Therefore, as described herein, various embodiments provide a shape memory alloy (SMA) cartridge for use in providing controllable compression. The SMA cartridge includes first and second end caps, each of the first and second end caps being coupled to a passive material. One or more SMA coils extend between the first and second end caps. The SMA coils have a trained state and a deformed state, where the SMA coils are in the deformed state when a stimulus is provided thereto and the SMA coils are in the trained state when the stimulus is removed therefrom. The first end cap and the second end cap include a locking mechanism to automatically lock the first and second end caps in a fixed position relative to one another when the SMA coils are contracted.

Reference herein to "one embodiment" or "an embodiment" means that a particular feature, structure, or characteristic described in connection with the embodiment can be included in at least one embodiment of the claimed subject matter. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the words "exemplary" and "illustrative" are used herein to mean serving as an example, instance, or illustration. Any aspect or design described herein as "exemplary" or "illustrative" is not necessarily to be construed as preferred or advantageous over other aspects or designs. Rather, use of the words "exemplary" and "illustrative" is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

To the extent directional terms are used in the specification and claims (e.g., upper, lower, parallel, perpendicular, etc.), these terms are merely intended to assist in describing the embodiments and are not intended to limit the claims in any way. Such terms, do not require exactness (e.g., exact perpendicularity or exact parallelism, etc.), but instead it is intended that normal tolerances and ranges apply. Similarly, unless explicitly stated otherwise, each numerical value and range should be interpreted as being approximate as if the word "about", "substantially" or "approximately" preceded the value of the value or range.

Some embodiments might be implemented in the form of methods and apparatuses for practicing those methods. Further, as would be apparent to one skilled in the art, various functions of circuit elements might also be implemented as processing blocks in a software program. Described embodiments might also be implemented in the form of program code embodied in tangible media, such as magnetic recording media, hard drives, floppy diskettes, magnetic tape media, optical recording media, compact discs (CDs), digital versatile discs (DVDs), solid state memory, hybrid magnetic and solid state memory, or any other machine-readable storage medium, wherein, when the program code is loaded into and executed by a machine, such as a computer, the machine becomes an apparatus for practicing the claimed invention. Described embodiments might also be implemented in the form of program code, for example, whether stored in a storage medium, loaded into and/or executed by a machine, or transmitted over some transmission medium or carrier, such as over electrical wiring or cabling, through fiber optics, or via electromagnetic radiation, wherein, when the program code is loaded into and executed by a machine, such as a computer, the machine becomes an apparatus for practicing the claimed invention. When implemented on a processing device, the program code segments combine with the processor to provide a unique device that operates analogously to specific logic circuits. Such processing devices might include, for example, a general purpose microprocessor, a digital signal processor (DSP), a reduced instruction set computer (RISC), a complex instruction set computer (CISC), an application specific integrated circuit (ASIC), a field programmable gate array (FPGA), a programmable logic array (PLA), a microcontroller, an embedded controller, a multi-core processor, and/or others, including combinations of the above. Described embodiments might also be implemented in the form of a bitstream or other sequence of signal values electrically or optically transmitted through a medium, stored magnetic-field variations in a magnetic recording medium, etc., generated using a method and/or an apparatus as recited in the claims.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements. Signals and corresponding nodes or ports may be referred to by the same name and are interchangeable for purposes here.

It should be understood that the steps of the methods set forth herein are not necessarily required to be performed in the order described, and the order of the steps of such methods should be understood to be merely illustrative. Likewise, additional steps may be included in such methods, and certain steps may be omitted or combined, in methods consistent with various embodiments.

It will be further understood that various changes in the details, materials, and arrangements of the parts that have been described and illustrated herein might be made by those skilled in the art without departing from the scope of the following claims.

We claim:

1. A shape memory alloy (SMA) cartridge for use in providing controllable compression comprising:
   first and second end caps, each of the first and second end caps coupled to a passive material; and
   one or more SMA coils extending between the first and second end caps, the SMA coils having a trained state and a deformed state, wherein the SMA coils are in the deformed state when a stimulus is provided thereto and wherein the SMA coils are in the trained state when the stimulus is removed therefrom;
   wherein the first end cap and the second end cap comprise a locking mechanism to automatically lock the first and second end caps in a fixed position relative to one another when the SMA coils are contracted.

2. The SMA cartridge of claim 1, wherein the trained state of the SMA coils comprises a non-contracted state of the SMA coils, and the deformed state of the SMA coils comprises a contracted state of the SMA coils.

3. The SMA cartridge of claim 2, wherein, when locked, the locking mechanism holds the cartridge in the contracted state if the stimulus is removed.

4. The SMA cartridge of claim 1, further comprising:
   a central spacer disposed between the first and second end caps to hold the one or more SMA coils in a fixed spaced relation to one another in a region between the end caps, wherein the locking mechanism locks the first and second end caps to the central spacer.

5. The SMA cartridge of claim 1, wherein:
   the one or more SMA coils comprise a single SMA coil.

6. The SMA cartridge of claim 1, wherein:
   the one or more SMA coils comprise multiple SMA coils arranged in parallel.

7. The SMA cartridge of claim 1, wherein:
   the first and second end caps each include interface structures for use in coupling each of the first and second end caps to the passive material.

8. The SMA cartridge of claim 7, wherein the interface structures comprise attachment means configured to couple each of the first and second end caps to the passive material.

9. The SMA cartridge of claim 7, wherein the interface structures comprise at least one lug and at least one well, the at least one lug configured to be received by a corresponding one of the at least one well, thereby retaining the passive material therein.

10. The SMA cartridge of claim 7, wherein the passive material comprises a textile material.

11. The SMA cartridge of claim 1, wherein the passive material comprises one or more hard or semi-hard passive structures.

12. The SMA cartridge of claim 1, wherein:
   the locking mechanism comprises at least one arm having a locking tab disposed thereon, the locking tab configured to engage a corresponding surface of at least one of a central spacer and one of the first and second end caps when the SMA coils are in the contracted state.

13. The SMA cartridge of claim 12, wherein:
   the locking mechanism configured to release, permitting the SMA cartridge to be unlocked from the contracted state.

14. The SMA cartridge of claim 1, wherein the SMA cartridge comprises a cover enclosing the one or more SMA coils.

15. The SMA cartridge of claim 1, wherein the SMA cartridge is disposed to form an active seam of a compression garment.

16. The SMA cartridge of claim 15, wherein the compression garment comprises one of: a bandage, a tourniquet, a mechanical counter-pressure (MCP) space suit, a compressive shirt, compressive pants, a compressive full body suit, and a compressive sleeve configured to receive a body part of interest.

17. The SMA cartridge of claim 15, wherein the compression garment comprises a tri-axial braid structure.

18. The SMA cartridge of claim 1, wherein the SMA coil comprises a nickel and titanium (NiTi) alloy.

19. The SMA cartridge of claim 1, wherein the SMA cartridge comprises at least one material, the at least one material comprising at least one of Acrylonitrile Butadiene Styrene (ABS) and a Fused Deposition Modeling (FDM) thermoplastic.

20. A compression garment comprising:
   at least one passive member for surrounding a body part of interest; and
   at least one shape memory alloy (SMA) cartridge coupled to ends of the passive member for use in providing controllable compression to the body part of interest, the at least one SMA cartridge comprising:
      first and second end caps, each of the first and second end caps coupled to a passive material; and
      one or more SMA coils extending between the first and second end caps, the SMA coils having a trained state and a deformed state, wherein the SMA coils are in the deformed state when a stimulus is provided thereto and wherein the SMA coils are in the trained state when the stimulus is removed therefrom;
      wherein the first end cap and the second end cap comprise a locking mechanism to automatically lock the first and second end caps in a fixed position relative to one another when the SMA coils are contracted.

21. A method of making a shape memory alloy (SMA) cartridge for use in providing controllable compression, the SMA cartridge comprising first and second end caps configured to be coupled to a passive material and one or more SMA coils extending between the first and second end caps, the first and second end caps comprising a locking mechanism to automatically lock the first and second end caps in a fixed position relative to one another when the SMA coils are contracted, the method comprising:
   generating the first and second end caps using at least one material, the first and second end caps having at least one cavity configured to receive the one or more SMA coils;
   pausing, at a predetermined point of the generating step, the generating of the first and second end caps and while paused, interlacing the one or more SMA coils into the at least one cavity of each of the first and second end caps; and
   resuming and completing the generating step.

22. The method of claim 21, wherein the step of generating is performed by three-dimensional (3D) printing.

23. The method of claim 21, wherein the at least one material comprises at least one of Acrylonitrile Butadiene Styrene (ABS) and a Fused Deposition Modeling (FDM) thermoplastic.

24. The method of claim 21, further comprising:
  encasing the one or more SMA coils in the at least one material.

\* \* \* \* \*